(12) United States Patent
DeHennis et al.

(10) Patent No.: US 12,016,684 B2
(45) Date of Patent: Jun. 25, 2024

(54) ENVIRONMENTAL DETECTION AND/OR TEMPERATURE COMPENSATION IN AN ANALYTE MONITORING SYSTEM

(71) Applicant: Senseonics, Incorporated, Germantown, MD (US)

(72) Inventors: Andrew DeHennis, Germantown, MD (US); Ravi Rastogi, Columbia, MD (US); Kamuran Turksoy, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 763 days.

(21) Appl. No.: 16/671,291

(22) Filed: Nov. 1, 2019

(65) Prior Publication Data

US 2020/0138345 A1 May 7, 2020

Related U.S. Application Data

(60) Provisional application No. 62/850,769, filed on May 21, 2019, provisional application No. 62/754,780, filed on Nov. 2, 2018.

(51) Int. Cl.
*A61B 5/145* (2006.01)
*A61B 5/00* (2006.01)
(Continued)

(52) U.S. Cl.
CPC ............ *A61B 5/14532* (2013.01); *A61B 5/01* (2013.01); *A61B 5/1116* (2013.01); *A61B 5/72* (2013.01);
(Continued)

(58) Field of Classification Search
CPC .............. A61B 5/14507; A61B 5/1451; A61B 5/14514; A61B 5/14517; A61B 5/14521
See application file for complete search history.

(56) References Cited

U.S. PATENT DOCUMENTS 8,660,627 B2  2/2014  Say et al.
9,149,220 B2  10/2015  Bohm et al.
(Continued)

FOREIGN PATENT DOCUMENTS

EP   2 305 105 B1   5/2012
EP   2770907 B1     7/2018
JP   2017-148583 A  8/2017

*Primary Examiner* — Jacqueline Cheng
*Assistant Examiner* — Jairo H Portillo
(74) *Attorney, Agent, or Firm* — Rothwell, Figg, Ernst & Manbeck, P.C.

(57) ABSTRACT

An analyte monitoring system may include an analyte sensor and a transceiver. The analyte sensor may include one or more sensors and a transceiver interface. The one or more sensors may be configured to generate sensor measurements indicative of an analyte level in a first medium. The sensors may include a temperature transducer configured to generate a sensor temperature measurement, and the sensor measurements may include the sensor temperature measurement. The transceiver interface may be configured to convey the sensor measurements. The transceiver may include a sensor interface and a processor. The sensor interface may be configured to receive the sensor measurements conveyed by the analyte sensor. The processor may be configured to adjust the sensor temperature measurement and calculate an analyte level in a second medium using at least the adjusted sensor temperature measurement and one or more of the sensor measurements.

34 Claims, 9 Drawing Sheets

(51) Int. Cl.
*A61B 5/01* (2006.01)
*A61B 5/11* (2006.01)

(52) U.S. Cl.
CPC ...... *A61B 5/742* (2013.01); *A61B 2560/0252* (2013.01)

(56) References Cited

U.S. PATENT DOCUMENTS

| | | | |
|---|---|---|---|
| 9,289,179 B2 | 5/2016 | Hayter et al. | |
| 9,414,775 B2 | 8/2016 | Colvin, Jr. et al. | |
| 9,693,714 B2 | 7/2017 | DeHennis et al. | |
| 9,743,872 B2 | 8/2017 | Hayter et al. | |
| 9,801,575 B2 | 10/2017 | Bohm et al. | |
| 9,808,190 B2 | 11/2017 | Bohm et al. | |
| 9,848,809 B2 | 12/2017 | Bohm et al. | |
| 10,004,442 B2 | 6/2018 | Bohm et al. | |
| 10,028,686 B2 | 7/2018 | Hayter | |
| 10,111,609 B2 | 10/2018 | Schmelzeisen-Redeker et al. | |
| 10,327,688 B2 | 6/2019 | Bohm et al. | |
| 10,448,873 B2 | 10/2019 | Bohm et al. | |
| 10,555,695 B2 | 2/2020 | Bohm et al. | |
| 10,561,354 B2 | 2/2020 | Bohm et al. | |
| 10,610,141 B2 | 4/2020 | Bohm et al. | |
| 10,624,568 B2 | 4/2020 | Bohm et al. | |
| 10,682,084 B2 | 6/2020 | Bohm et al. | |
| 10,722,162 B2 | 7/2020 | Bohm et al. | |
| 10,835,162 B2 | 11/2020 | Bohm et al. | |
| 10,980,461 B2 | 4/2021 | Simpson et al. | |
| 2008/0275318 A1* | 11/2008 | Lastovich | A61B 5/14532 600/316 |
| 2008/0288180 A1* | 11/2008 | Hayter | A61B 5/1473 702/23 |
| 2011/0191059 A1* | 8/2011 | Farrell | G01K 7/427 702/130 |
| 2011/0272294 A1* | 11/2011 | Fujiwara | G01N 27/3272 205/792 |
| 2012/0179017 A1 | 7/2012 | Satou et al. | |
| 2012/0262298 A1 | 10/2012 | Bohm et al. | |
| 2012/0265035 A1 | 10/2012 | Bohm et al. | |
| 2012/0265036 A1 | 10/2012 | Estes et al. | |
| 2012/0265037 A1 | 10/2012 | Bohm et al. | |
| 2013/0197847 A1 | 8/2013 | Tsukada et al. | |
| 2013/0211213 A1 | 8/2013 | DeHennis et al. | |
| 2013/0241745 A1 | 9/2013 | Colvin, Jr. et al. | |
| 2013/0267802 A1 | 10/2013 | Markle et al. | |
| 2014/0018644 A1 | 1/2014 | Colvin, Jr. et al. | |
| 2014/0114153 A1 | 4/2014 | Bohm et al. | |
| 2014/0114156 A1 | 4/2014 | Bohm et al. | |
| 2014/0350359 A1 | 11/2014 | Tankiewicz et al. | |
| 2015/0123641 A1 | 5/2015 | Dalton et al. | |
| 2015/0141770 A1 | 5/2015 | Rastogi et al. | |
| 2016/0018246 A1 | 1/2016 | Bohm et al. | |
| 2016/0073941 A1 | 3/2016 | Bohm et al. | |
| 2016/0157758 A1 | 6/2016 | Bohm et al. | |
| 2016/0198986 A1 | 6/2016 | Bohm et al. | |
| 2017/0055906 A1 | 3/2017 | Bremer | |
| 2017/0119288 A1 | 5/2017 | DeHennis et al. | |
| 2017/0281092 A1 | 10/2017 | Burnette et al. | |
| 2017/0350878 A1 | 12/2017 | Holmes et al. | |
| 2018/0008174 A1 | 1/2018 | Bohm et al. | |
| 2018/0042530 A1 | 2/2018 | Bohm et al. | |
| 2018/0125364 A1 | 5/2018 | DeHennis | |
| 2018/0153454 A1 | 6/2018 | Hayter et al. | |
| 2018/0271415 A1 | 9/2018 | Bohm et al. | |
| 2018/0279923 A1 | 10/2018 | Chen et al. | |
| 2018/0279928 A1 | 10/2018 | Bohm et al. | |
| 2019/0212323 A1* | 7/2019 | Gupta | G16C 20/20 |
| 2019/0261902 A1 | 8/2019 | Bohm et al. | |
| 2019/0261903 A1 | 8/2019 | Bohm et al. | |
| 2019/0320948 A1 | 10/2019 | Bohm et al. | |
| 2019/0320949 A1 | 10/2019 | Bohm et al. | |
| 2019/0336051 A1 | 11/2019 | Bohm et al. | |
| 2019/0350499 A1 | 11/2019 | Bohm et al. | |
| 2019/0357817 A1 | 11/2019 | Bohm et al. | |
| 2019/0380627 A1 | 12/2019 | Bohm et al. | |
| 2020/0022626 A1 | 1/2020 | Bohm et al. | |
| 2020/0037934 A1 | 2/2020 | Bohm et al. | |
| 2020/0037935 A1 | 2/2020 | Bohm et al. | |
| 2020/0037936 A1 | 2/2020 | Bohm et al. | |
| 2021/0000394 A1 | 1/2021 | Bohm et al. | |
| 2021/0038128 A1 | 2/2021 | Bohm et al. | |
| 2021/0038129 A1 | 2/2021 | Bohm et al. | |
| 2021/0068720 A1 | 3/2021 | Bohm et al. | |
| 2021/0076989 A1 | 3/2021 | Bohm et al. | |
| 2021/0369149 A1 | 12/2021 | Bohm et al. | |

\* cited by examiner

ENVIRONMENTAL DETECTION AND/OR TEMPERATURE COMPENSATION IN AN ANALYTE MONITORING SYSTEM

CROSS-REFERENCE TO RELATED APPLICATION

The present application claims the benefit of priority to U.S. Provisional Application Ser. No. 62/850,769, filed on May 21, 2019, and U.S. Provisional Application Ser. No. 62/754,780, filed on Nov. 2, 2018, which are incorporated herein by reference in their entirety.

BACKGROUND

Field of Invention

Aspects of the present invention relate to systems and methods for analyte monitoring. Specifically, aspects of the present invention may relate to environmental detection and/or temperature compensation in an analyte monitoring system. More specifically, the temperature compensation may be lag cognizant.

Discussion of the Background

The prevalence of diabetes mellitus continues to increase in industrialized countries, and projections suggest that this figure will rise to 4.4% of the global population (366 million individuals) by the year 2030. Glycemic control is a key determinant of long-term outcomes in patients with diabetes, and poor glycemic control is associated with retinopathy, nephropathy and an increased risk of myocardial infarction, cerebrovascular accident, and peripheral vascular disease requiring limb amputation. Despite the development of new insulins and other classes of antidiabetic therapy, roughly half of all patients with diabetes do not achieve recommended target hemoglobin A1c (HbA1c) levels<7.0%.

Frequent self-monitoring of blood glucose (SMBG) is necessary to achieve tight glycemic control in patients with diabetes mellitus, particularly for those requiring insulin therapy. However, current blood (finger-stick) glucose tests are burdensome, and, even in structured clinical studies, patient adherence to the recommended frequency of SMBG decreases substantially over time. Moreover, finger-stick measurements only provide information about a single point in time and do not yield information regarding intraday fluctuations in blood glucose levels that may more closely correlate with some clinical outcomes.

Continuous glucose monitors (CGMs) have been developed in an effort to overcome the limitations of finger-stick SMBG and thereby help improve patient outcomes. These systems enable increased frequency of glucose measurements and a better characterization of dynamic glucose fluctuations, including episodes of unrealized hypoglycemia. Furthermore, integration of CGMs with automated insulin pumps allows for establishment of a closed-loop "artificial pancreas" system to more closely approximate physiologic insulin delivery and to improve adherence.

Monitoring real-time analyte measurements from a living body via wireless analyte monitoring sensor(s) may provide numerous health and research benefits. There is a need to enhance such analyte monitoring systems via innovations.

SUMMARY

One aspect of the invention may provide an analyte monitoring system including an analyte sensor and a transceiver. The analyte sensor may include one or more sensor elements and a transceiver interface. The one or more sensor elements may be configured to generate one or more sensor measurements indicative of an analyte level in a first medium. The transceiver interface may be configured to convey the one or more sensor measurements. The transceiver may include a sensor interface, one or more environmental sensors, and a processor. The sensor interface may be configured to receive the one or more sensor measurements conveyed by the analyte sensor. The one or more environmental sensors may be configured to generate one or more environment measurements. The processor may be configured to calculate an analyte level in a second medium using at least the one or more sensor measurements and the one or more environmental measurements.

Another aspect of the invention may provide an analyte monitoring system including an analyte sensor, one or more environmental sensors, and a transceiver. The analyte sensor may include one or more sensor elements and a transceiver interface. The one or more sensor elements may be configured to generate one or more sensor measurements indicative of an analyte level in a first medium. The transceiver interface may be configured to convey the one or more sensor measurements. The one or more environmental sensors may be configured to generate one or more environment measurements. The transceiver may be configured to receive the one or more environmental measurements. The transceiver may include a sensor interface and a processor. The sensor interface may be configured to receive the one or more sensor measurements conveyed by the analyte sensor. The processor may be configured to calculate an analyte level in a second medium using at least the one or more sensor measurements and the one or more environmental measurements.

In some aspects, the one or more environmental sensors may include a posture detector, the one or more environmental measurements may include one or more posture measurements indicative of a posture of a user of the transceiver, and the processor may be configured to calculate the analyte level in the second medium using at least the one or more sensor measurements and the one or more posture measurements. In some aspects, the posture detector may include an accelerometer and a barometer, the one or more posture measurements may include one or more acceleration measurements and one or more atmospheric measurements, and calculating the analyte level in the second medium using at least the one or more sensor measurements and the one or more posture measurements may include: (i) calculating a posture of the user of the transceiver using at least the one or more posture measurements; and (ii) calculating the analyte level in the second medium using at least the one or more sensor measurements and the calculated posture. In some aspects, calculating the analyte level in the second medium using at least the one or more sensor measurements and the calculated posture may include: adjusting one or more parameters of a conversion function based on at least the calculated posture; and using the adjusted conversion function and the one or more sensor measurements to calculate the analyte level in the second medium.

In some aspects, the one or more environmental sensors may include a pressure sensor, the one or more environmental measurements may include one or more pressure measurements indicative of pressure on the transceiver, and the processor may be configured to calculate the analyte level in the second medium using at least the one or more sensor measurements and the one or more pressure measurements. In some aspects, the pressure sensor may include a button. In some aspects, calculating the analyte level in the second medium using at least the one or more sensor measurements and the one or more pressure measurements may include: adjusting one or more parameters of a conversion function based on at least the one or more pressure measurements; and using the adjusted conversion function and the one or more sensor measurements to calculate the analyte level in the second medium.

In some aspects, the one or more environmental sensors may include an accelerometer, the one or more environmental measurements may include one or more acceleration measurements generated by the accelerometer, and the processor may be configured to calculate the analyte level in the second medium using at least the one or more sensor measurements and the one or more acceleration measurements. In some aspects, calculating the analyte level in the second medium using at least the one or more sensor measurements and the one or more acceleration measurements may include: determining whether a shock to the transceiver has occurred using at least the one or more acceleration measurements; and calculating the analyte level in the second medium using at least the one or more sensor measurements and the determination of whether a shock to the transceiver has occurred. In some aspects, calculating the analyte level in the second medium using at least the one or more sensor measurements and the determination of whether a shock to the transceiver has occurred may include: adjusting one or more parameters of a conversion function based on at least the determination of whether a shock to the transceiver has occurred; and using the adjusted conversion function and the one or more sensor measurements to calculate the analyte level in the second medium.

In some aspects, the one or more environmental sensors may include a temperature sensor, the one or more environmental measurements may include one or more temperature measurements generated by the temperature sensor, and the processor may be configured to calculate the analyte level in the second medium using at least the one or more sensor measurements and the one or more temperature measurements. In some aspects, calculating the analyte level in the second medium using at least the one or more sensor measurements and the one or more temperature measurements may include: adjusting at least a sensor measurement of the one or more sensor measurements based on the one or more temperature measurements; and using the one or more sensor measurements including the adjusted sensor measurement to calculate the analyte level in the second medium.

In some aspects, the transceiver may be further configured to use at least one or more of the one or more environmental measurements to adjust a sampling frequency of one or more of the one or more environmental sensors. In some aspects, the transceiver may be further configured to: use at least one or more of the one or more environmental measurements to determine whether an environmental event has occurred; and, if the transceiver determines that the environmental event has occurred, cause the transceiver or a display device to display an icon indicative of the environmental event.

Another aspect of the invention may provide a method including using one or more sensor elements of an analyte sensor to generate one or more sensor measurements indicative of an analyte level in a first medium. The method may include using a transceiver interface of the analyte sensor to convey the one or more sensor measurements. The method may include using a sensor interface of a transceiver to receive the one or more sensor measurements conveyed by the analyte sensor. The method may include using one or more environmental sensors of the transceiver to generate one or more environment measurements. The method may include using the transceiver to calculate an analyte level in a second medium using at least the one or more sensor measurements and the one or more environmental measurements.

In some aspects, the one or more environmental sensors may include a posture detector, the one or more environmental measurements may include one or more posture measurements indicative of a posture of a user of the transceiver, and the transceiver may calculate the analyte level in the second medium using at least the one or more sensor measurements and the one or more posture measurements. In some aspects, the posture detector may include an accelerometer and a barometer, the one or more posture measurements may include one or more acceleration measurements and one or more atmospheric measurements, and calculating the analyte level in the second medium using at least the one or more sensor measurements and the one or more posture measurements may include: calculating a posture of the user of the transceiver using at least the one or more posture measurements; and calculating the analyte level in the second medium using at least the one or more sensor measurements and the calculated posture. In some aspects, calculating the analyte level in the second medium using at least the one or more sensor measurements and the calculated posture may include: adjusting one or more parameters of a conversion function based on at least the calculated posture; and using the adjusted conversion function and the one or more sensor measurements to calculate the analyte level in the second medium.

In some aspects, the one or more environmental sensors may include a pressure sensor, the one or more environmental measurements may include one or more pressure measurements indicative of pressure on the transceiver, and the transceiver may calculate the analyte level in the second medium using at least the one or more sensor measurements and the one or more pressure measurements. In some aspects, calculating the analyte level in the second medium using at least the one or more sensor measurements and the one or more pressure measurements may include: adjusting one or more parameters of a conversion function based on at least the one or more pressure measurements; and using the adjusted conversion function and the one or more sensor measurements to calculate the analyte level in the second medium.

In some aspects, the one or more environmental sensors may include an accelerometer, the one or more environmental measurements may include one or more acceleration measurements, and the transceiver may calculate the analyte level in the second medium using at least the one or more sensor measurements and the one or more acceleration measurements. In some aspects, calculating the analyte level in the second medium using at least the one or more sensor measurements and the one or more acceleration measurements may include: determining whether a shock to the transceiver has occurred using at least the one or more acceleration measurements; and calculating the analyte level in the second medium using at least the one or more sensor measurements and the determination of whether a shock to the transceiver has occurred. In some aspects, calculating the analyte level in the second medium using at least the one or more sensor measurements and the determination of whether a shock to the transceiver has occurred may include: adjusting one or more parameters of a conversion function based on at least the determination of whether a shock to the transceiver has occurred; and using the adjusted conversion function and the one or more sensor measurements to calculate the analyte level in the second medium.

In some aspects, the one or more environmental sensors may include a temperature sensor, the one or more environmental measurements may include one or more temperature measurements generated by the temperature sensor, and the processor may be configured to calculate the analyte level in the second medium using at least the one or more sensor measurements and the one or more temperature measurements. In some aspects, calculating the analyte level in the second medium using at least the one or more sensor measurements and the one or more temperature measurements may include: adjusting at least a sensor measurement of the one or more sensor measurements based on the one or more temperature measurements; and using the one or more sensor measurements including the adjusted sensor measurement to calculate the analyte level in the second medium.

In some aspects, the method may include using at least one or more of the one or more environmental measurements to adjust a sampling frequency of one or more of the one or more environmental sensors. In some aspects, the method may include using at least one or more of the one or more environmental measurements to determine that an environmental event has occurred, and displaying an icon indicative of the environmental event.

Still another aspect of the invention may provide an analyte monitoring system including an analyte sensor and a transceiver. The analyte sensor may include one or more sensor elements and a transceiver interface. The one or more sensor elements may be configured to generate sensor measurements indicative of an analyte level in a first medium. The sensor elements may include a temperature transducer configured to generate a sensor temperature measurement. The sensor measurements may include the sensor temperature measurement. The transceiver interface may be configured to convey the sensor measurements.

In some embodiments, the analyte sensor may further include a housing and an analyte indicator on or in at least a portion of an exterior surface of the sensor housing. In some embodiments, the sensor temperature measurement may be a measurement of temperature inside the housing of the analyte sensor, and the adjusted sensor temperature measurement may be an estimate of a temperature of the analyte indicator. In some embodiments, the adjusted sensor temperature measurement may account for a lag between the temperature inside the housing of the analyte sensor and the temperature of the analyte indicator.

In some embodiments, adjusting the sensor temperature measurement may include calculating a rate of change of the temperature of the analyte sensor using at least the sensor temperature measurement and one or more sensor temperature measurements received previously from the analyte sensor. In some embodiments, calculating the analyte level in the second medium using at least the adjusted sensor temperature measurement and the one or more of the sensor measurements may include calculating an analyte level in the first medium using at least the adjusted sensor temperature measurement and the one or more of the sensor measurements and calculating the analyte level in the second medium using at least the calculated analyte level in the first medium.

In some embodiments, the analyte monitoring system may further include a temperature sensor configured to generate a temperature measurement, and the processor may be configured to adjust the sensor temperature measurement using at least the temperature measurement generated by the temperature sensor. In some embodiments, the transceiver may include the temperature sensor. In some embodiments, the adjusted sensor temperature measurement may account for a lag between a temperature measured by the temperature sensor and the temperature of the analyte indicator. In some embodiments, adjusting the sensor temperature measurement may include calculating a rate of change of the temperature of the transceiver using at least the temperature measurement generated by the temperature sensor and one or more temperature measurements generated previously by the temperature sensor. In some embodiments, adjusting the sensor temperature measurement may include calculating the adjusted sensor temperature measurement using at least the temperature measurement generated by the temperature sensor and the calculated rate of change of the temperature of the transducer. In some embodiments, adjusting the sensor temperature measurement may include calculating a rate of change of the temperature of the analyte sensor using at least the sensor temperature measurement and one or more sensor temperature measurements received previously from the analyte sensor, and calculating the adjusted sensor temperature measurement may use at least the sensor temperature measurement, the calculated rate of change of the temperature of the analyte sensor, the temperature measurement generated by the temperature sensor, and the calculated rate of change of the temperature of the transducer.

Yet another aspect of the invention may provide a method including using one or more sensor elements of an analyte sensor to generate sensor measurements indicative of an analyte level in a first medium. The sensor elements may include a temperature transducer, and the sensor measurements may include a sensor temperature measurement generated by the temperature transducer. The method may include using a transceiver interface of the analyte sensor to convey the sensor measurements. The method may include using a sensor interface of a transceiver to receive the sensor measurements conveyed by the analyte sensor. The method may include using the transceiver to adjust the sensor temperature measurement. The method may include using the transceiver to calculate an analyte level in a second medium using at least the adjusted sensor temperature measurement and one or more of the sensor measurements.

In some embodiments, the analyte sensor may further include a housing and an analyte indicator on or in at least a portion of an exterior surface of the sensor housing, the sensor temperature measurement may be a measurement of temperature inside the housing of the analyte sensor, and the adjusted sensor temperature measurement may be an estimate of a temperature of the analyte indicator. In some embodiments, the adjusted sensor temperature measurement may account for a lag between the temperature inside the housing of the analyte sensor and the temperature of the analyte indicator.

In some embodiments, adjusting the sensor temperature measurement may include calculating a rate of change of the temperature of the analyte sensor using at least the sensor temperature measurement and one or more sensor temperature measurements received previously from the analyte sensor. In some embodiments, adjusting the sensor temperature measurement may include calculating the adjusted sensor temperature measurement using at least the sensor temperature measurement and the calculated rate of change of the temperature of the analyte sensor. In some embodiments, calculating the analyte level in the second medium using at least the adjusted sensor temperature measurement and the one or more of the sensor measurements may include calculating an analyte level in the first medium using at least the adjusted sensor temperature measurement and the one or more of the sensor measurements and calculating the analyte level in the second medium using at least the calculated analyte level in the first medium.

In some embodiments, the method may further include using a temperature sensor to generate a temperature measurement, wherein the processor is configured to adjust the sensor temperature measurement using at least the temperature measurement generated by the temperature sensor. In some embodiments, the adjusted sensor temperature measurement may account for a lag between a temperature measured by the temperature sensor and the temperature of the analyte indicator. In some embodiments, adjusting the sensor temperature measurement may include calculating a rate of change of the temperature of the transceiver using at least the temperature measurement generated by the temperature sensor and one or more temperature measurements generated previously by the temperature sensor. In some embodiments, adjusting the sensor temperature measurement may include calculating the adjusted sensor temperature measurement using at least the temperature measurement generated by the temperature sensor and the calculated rate of change of the temperature of the transducer. In some embodiments, adjusting the sensor temperature measurement may include calculating a rate of change of the temperature of the analyte sensor using at least the sensor temperature measurement and one or more sensor temperature measurements received previously from the analyte sensor, and calculating the adjusted sensor temperature measurement may use at least the sensor temperature measurement, the calculated rate of change of the temperature of the analyte sensor, the temperature measurement generated by the temperature sensor, and the calculated rate of change of the temperature of the transducer.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

DETAILED DESCRIPTION OF PREFERRED EMBODIMENTS

Figure 1A:
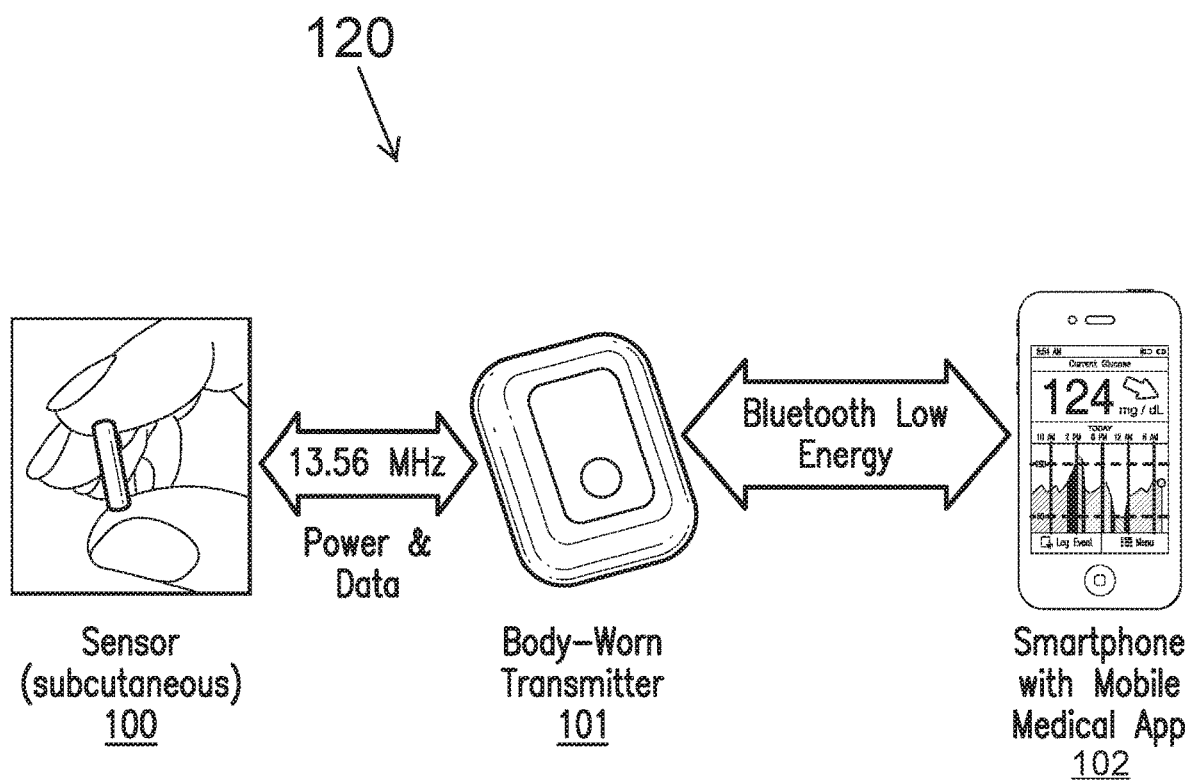
FIGS. 1A and 1B are schematic views illustrating an analyte monitoring system embodying aspects of the present invention.
Figure 1B:
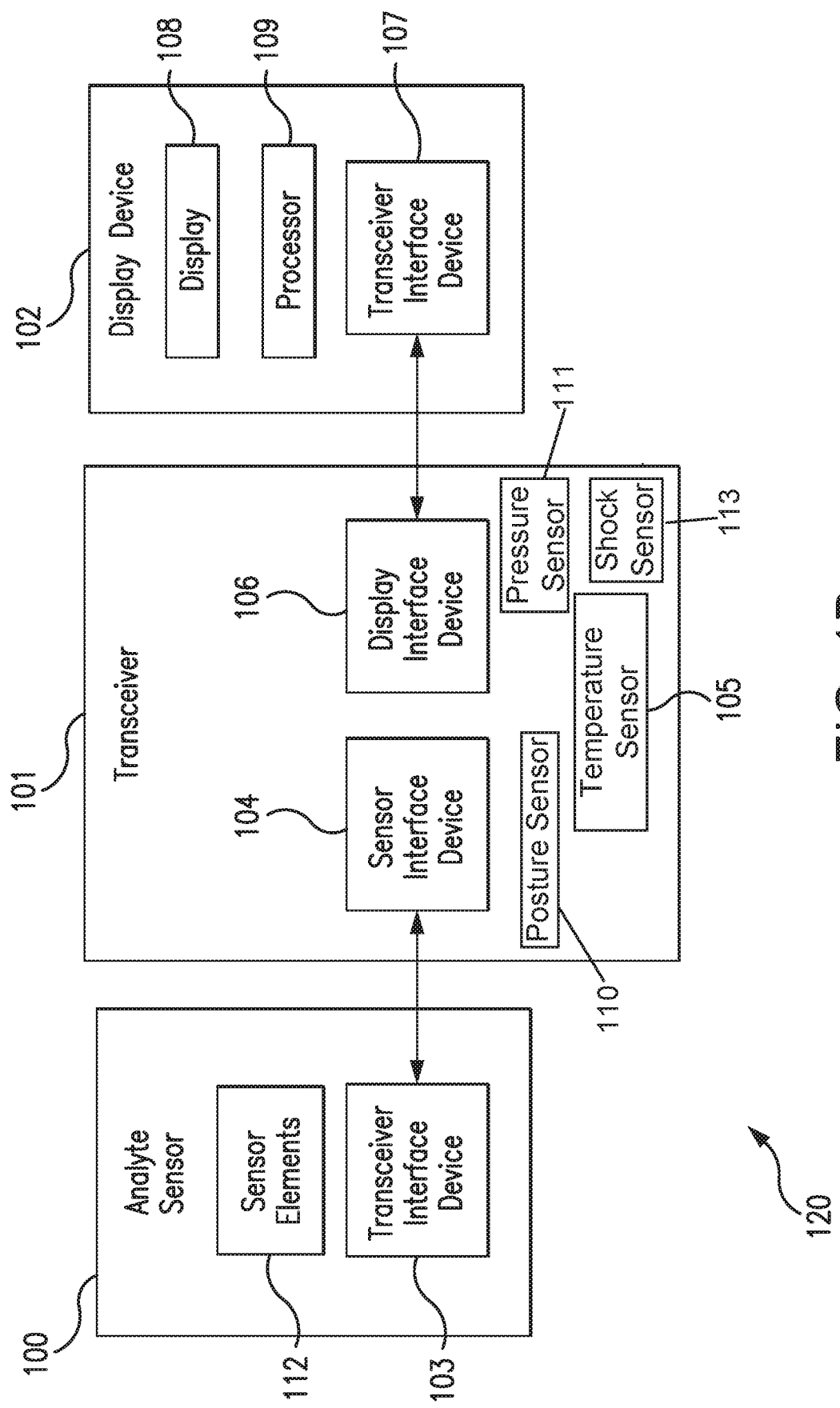

FIGS. 1A and 1B are schematic views of an exemplary analyte monitoring system 120 embodying aspects of the present invention. The analyte monitoring system 120 may be a continuous analyte monitoring system (e.g., a continuous glucose monitoring system). In some embodiments, as shown in FIGS. 1A and 1B, the system 120 may include one or more of an analyte sensor 100, a transceiver 101, and a display device 102. In some embodiments, the sensor 100 and transceiver 101 may include one or more of the structural and/or functional features described in one or more of U.S. Patent Application Publication No. 2013/0241745, U.S. Patent Application Publication No. 2013/0211213, U.S. Patent Application Publication No. 2014/0350359, U.S. Patent Application Publication No. 2014/0018644, and U.S. Patent Application Publication No. 2017/0119288, all of which are incorporated by reference in their entireties.

In some embodiments, as shown in FIG. 1A, the sensor 100 may be small, fully subcutaneously implantable sensor that measures analyte (e.g., glucose, oxygen, cardiac markers, low-density lipoprotein (LDL), high-density lipoprotein (HDL), or triglycerides) levels in a medium (e.g., interstitial fluid) of a living animal (e.g., a living human). However, this is not required, and, in some alternative embodiments, the sensor 100 may be a partially implantable (e.g., transcutaneous) sensor or a fully external sensor. In some embodiments, the transceiver 101 may be a handheld or body-worn transceiver (e.g., attached via an armband, wristband, waistband, or adhesive patch). In some embodiments, as shown in FIG. 1A, the transceiver 101 may remotely power and/or communicate with the sensor to initiate and receive the measurements (e.g., via near field communication (NFC)). However, this is not required, and, in some alternative embodiments, the transceiver 101 may power and/or communicate with the sensor 100 via one or more wired connections. In some non-limiting embodiments, the transceiver 101 may be a smartphone (e.g., an NFC-enabled smartphone). In some embodiments, the transceiver 101 may communicate information (e.g., one or more analyte levels) wirelessly (e.g., via a Bluetooth™ communication standard such as, for example and without limitation Bluetooth Low Energy) to a hand held application running on a display device 102 (e.g., smartphone).

In some embodiments, the transceiver 101 may convey (e.g., periodically, such as every two or five minutes, and/or upon user initiation) measurement commands (i.e., requests for measurement information) to the sensor 100. In some embodiments where the transceiver 101 is a handheld device, positioning (i.e., hovering or swiping/waving/passing) the transceiver 101 within range over the sensor implant site (i.e., within proximity of the sensor 100) may cause the transceiver 101 to automatically convey a measurement command to the sensor 100 and receive one or more sensor measurements conveyed by the sensor 100.

In some embodiments, as illustrated in FIG. 1B, the analyte sensor 100 may include a transceiver interface 103 that the analyte sensor 100 may use to communicate with the transceiver 101, and the transceiver 101 may include a sensor interface 104 that the transceiver 101 may use to communicate with the analyte sensor 100. In some non-limiting embodiments, the transceiver interface 103 and the sensor interface 104 may each include one or more inductive elements, such as, for example, one or more coils. In some embodiments, the sensor interface 104 of the transceiver 101 may generate an electromagnetic wave or electrodynamic field (e.g., by using a coil) to induce a current in a transceiver interface 103 of the sensor 100. In some non-limiting embodiments, the current induced in the transceiver interface 103 of the sensor 100 may be used to power the sensor 100. In some embodiments, the current induced in the transceiver interface 103 of the sensor 100 may additionally or alternatively be used for communication. For example, in some embodiments, the transceiver 101 may use the sensor interface 104 to convey data (e.g., commands) to the sensor 100. In some non-limiting embodiments, the transceiver 101 may use the sensor interface 104 to convey data by modulating the electromagnetic wave used to power the sensor 100 (e.g., by modulating the current flowing through a coil of the sensor interface 104 of the transceiver 101). In some embodiments the modulation in the electromagnetic wave generated by the sensor interface 104 of the transceiver 101 may be detected/extracted by the sensor 100 (e.g., by the transceiver interface 103 of the sensor 100). Moreover, the transceiver 101 may use the sensor interface 104 to receive sensor data (e.g., one or more sensor measurements) conveyed by the sensor 100. For example, in some non-limiting embodiments, the transceiver 101 may receive sensor data by detecting modulations in the electromagnetic wave generated by the transceiver interface 103 of the sensor 100, e.g., by detecting modulations in the current flowing through a coil of the sensor interface 104 of the transceiver 101.

In some non-limiting embodiments, as shown in FIG. 1B, the analyte sensor 100 may include one or more sensor elements 112. In some non-limiting embodiments, the sensor elements 112 may include an analyte indicator. In some embodiments, the analyte indicator may include one or more indicator molecules having one or more detectable properties that vary in accordance with the amount, level, or concentration of the analyte in proximity to the analyte indicator.

In some embodiments, the sensor 100 may be an optical sensor. However, this is not required, and, in one or more alternative embodiments, the sensor 100 may be a different type of analyte sensor, such as, for example, an electrochemical sensor, a diffusion sensor, or a pressure sensor. Also, although in some embodiments the analyte sensor 100 may be a fully implantable sensor, this is not required, and, in some alternative embodiments, the sensor 100 may be a transcutaneous sensor having a wired connection to the transceiver 101. For example, in some alternative embodiments, the sensor 100 may be located in or on a transcutaneous needle (e.g., at the tip thereof). In these embodiments, instead of the sensor 100 and transceiver 101 wirelessly communicating using the transceiver interface 103 and sensor interface 104, the transceiver interface 103 and sensor interface 104 may enable wired communication between the sensor 100 and transceiver 101. In some non-limiting transcutaneous embodiments, one or more wires may be connected between the transceiver 101 and the transceiver transcutaneous needle that includes the sensor 100. For another example, in some alternative embodiments, the sensor 100 may be located in a catheter (e.g., for intravenous blood glucose monitoring) and may communicate (wirelessly or using wires) with the transceiver 101.

In some embodiments, as illustrated in FIG. 1B, the transceiver 101 may include one or more environmental sensors configured to generate one or more environmental measurements. In some embodiments, the one or more environmental sensors may include one or more of: (i) one or more posture sensors 110, (ii) one or more pressure sensors 111, (iii) one or more shock sensors 113, and (iv) one or more temperature sensors 105. In some embodiments, the one or more posture sensors 110 may generate one or more posture measurements indicative of the posture of a user of the transceiver 101. In some embodiments, the one or more posture sensors 110 may include an accelerometer and a barometer. In some embodiments, the one or more pressure sensors 111 may generate one or more pressure measurements indicative of pressure on the transceiver 101 (e.g., due to the user of the transceiver 101 laying on the transceiver 101). In some non-limiting embodiments, the one or more pressure measurements may indicate how much pressure is being applied to the transceiver 101. In some alternative embodiments, the one or more pressure measurements may simply indicate whether the user is laying on the transceiver 101 (e.g., yes or no). In some embodiments, the one or more pressure sensors 111 may include one or more buttons (e.g., one or more buttons on the surface of the transceiver 101 that faces the user). In some embodiments, the one or more shock sensors 113 may include an accelerometer and generate one or more acceleration measurements. In some embodiments, the one or more acceleration measurements may be indicate of whether a shock to the transceiver 101 has occurred. In some embodiments, the one or more temperature sensors 105 may generate one or more temperature measurements indicative of the temperature of the transceiver 101.

In some embodiments, the transceiver 101 may receive one or more measurements conveyed by the analyte sensor 100. In some embodiments, the transceiver 101 may calculate one or more analyte levels using at least the one or more measurements conveyed by the analyte sensor 100. In some embodiments, the transceiver 101 may additionally use one or more environmental measurements to calculate the one or more analyte levels. However, it is not required that the transceiver 101 perform the analyte level calculations itself, and, in some alternative embodiments, the transceiver 101 may instead convey/relay the measurement information received conveyed by the sensor 100 to another device (e.g., display device 102) for calculation of analyte levels (e.g., by a mobile medical application executing on the display device 102). In some non-limiting embodiments, the analyte level calculation may include one or more features described in U.S. Patent Application Publication No. 2014/0018644, which is incorporated by reference in its entirety.

In some embodiments, the transceiver 101 and/or display device 102 may be configured to generate one or more alerts, alarms, or notifications based on the one or more analyte levels and/or the one or more environmental measurements. In some embodiments, one or more of the transceiver 101 and the display device 102 may communicate the alerts, alarms, and/or notifications to a user. In some embodiments, the alerts, alarms, and/or notifications may be visual, audible, and/or vibratory in nature.

In some embodiments, as shown in FIG. 1B, the transceiver 101 may include a display interface 106 that the transceiver 101 may use to communicate with the display device 102, and the display device 102 may include a transceiver interface 107 that the display device 102 may use to communicate with the transceiver 101. In some embodiments, the display interface 106 and transceiver interface 107 may enable wireless communication between the transceiver 101 and display device 102. In some embodiments, the display interface 106 and transceiver interface 107 may communicate using one or more wireless protocols. In some non-limiting embodiments, the wireless protocols may include a Bluetooth protocol (e.g., an Bluetooth Low Energy (BLE) protocol). In some embodiments, the transceiver 101 may use the display interface 106 to communicate one or more analyte measurements, one or more analyte levels, one or more alerts, alarms, or notifications, and/or one or more environmental measurements to the display device 102.

In some embodiments, the system 120 may include one or more displays. For example, in some embodiments, as shown in FIG. 1B, the display device 102 may include a display 108 configured to display one or more analyte levels, one or more alerts, alarms, or notifications, and/or one or more environmental measurements. In some embodiments, the transceiver 101 may additionally or alternatively include a display configured to display one or more analyte levels, one or more alerts, alarms, or notifications, and/or one or more environmental measurements.

In some embodiments, as shown in FIG. 1B, the transceiver 101 may include a display interface 106 configured to convey information (e.g., alerts and/or analyte levels) to one or more display devices 102. In some embodiments, a display device 102 may be a portable and/or handheld device. In some embodiments, the display device 102 may be a smartphone. However, this is not required, and, in some alternative embodiments, the display device 102 may be a laptop computer, tablet, notebook, personal data assistant ("PDA"), personal computer, or a dedicated analyte monitoring display device. In some embodiments, the display device 102 may include a transceiver interface 107, which may be configured to communicate with the display interface 106 of the transceiver 101 through a wired or wireless connection. In some embodiments, the display device 102 may include a processor 109, and the processor 109 may be configured to execute a mobile medical application stored in a memory of the display device 102.

Figure 2:
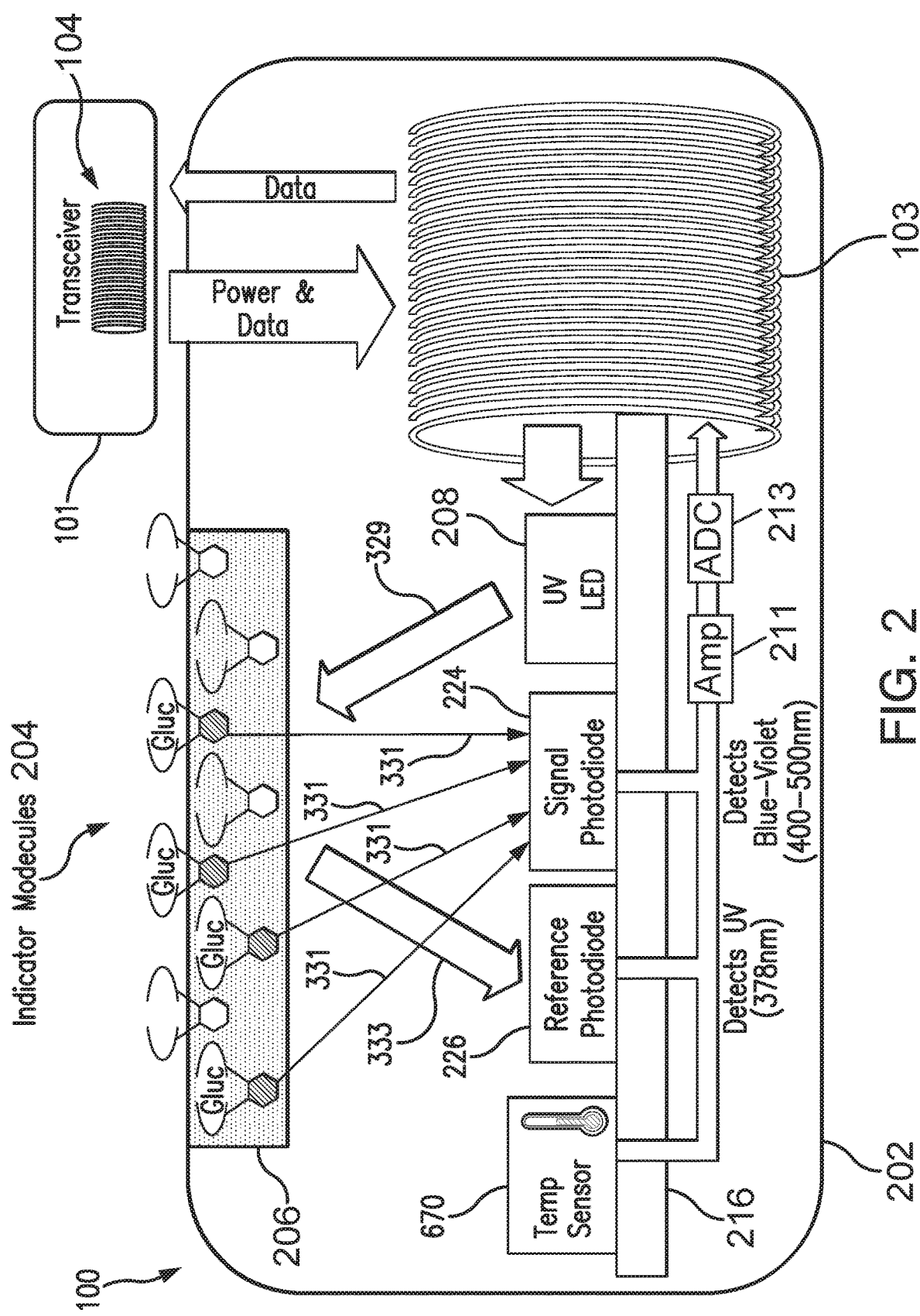
FIG. 2 is a schematic view illustrating a sensor and transceiver of an analyte monitoring system embodying aspects of the present invention.

FIG. 2 is a schematic view illustrating a non-limiting example of the sensor 100 and transceiver 101 of the analyte monitoring system 120 according some embodiments of the invention. In some embodiments, the sensor elements 112 of the sensor 100 may include one or more analyte indicators 206, one or more light sources 208, one or more photodetectors 224, 226, one or more temperature transducers 670, a substrate 216, an amplifier 211, and/or an analog-to-digital converter (ADC) 213. In some non-limiting embodiments, as illustrated in FIG. 2, the sensor 100 may be encased in a sensor housing 202 (i.e., body, shell, capsule, or encasement), which may be rigid and biocompatible. In some embodiments, the analyte indicator 206 may be, for example and without limitation, a hydrogel or polymer graft coated, diffused, adhered, or embedded on or in at least a portion of the exterior surface of the sensor housing 202. In some embodiments, the analyte indicator 206 (e.g., polymer graft) of the sensor 100 may include indicator molecules 204 (e.g., fluorescent indicator molecules) exhibiting one or more detectable properties (e.g., optical properties) based on the amount or concentration of the analyte in proximity to the analyte indicator 206.

In some embodiments, as shown in FIG. 2, the light source 208 may emit excitation light 329 over a range of wavelengths that interact with the indicator molecules 204. In some embodiments, a photodetector 224 may be sensitive to emission light 331 (e.g., fluorescent light) emitted by the indicator molecules 204 such that a signal generated by the photodetector 224 in response thereto that is indicative of the level of emission light 331 of the indicator molecules 104 and, thus, the amount of analyte of interest (e.g., glucose). In some non-limiting embodiments, a photodetector 226 may be sensitive to excitation light 329 that is reflected from the analyte indicator 206 as reflection light 333. In some non-limiting embodiments, one or more of the photodetectors may be covered by one or more filters that allow only a certain subset of wavelengths of light to pass through (e.g., a subset of wavelengths corresponding to emission light 331 or a subset of wavelengths corresponding to reflection light 333) and reflect the remaining wavelengths. In some non-limiting embodiments, the temperature transducer 670 may output a signal indicative of the temperature inside the housing 202 of the sensor 100. In some non-limiting embodiments, the sensor 100 may include a drug-eluting polymer matrix that disperses one or more therapeutic agents (e.g., an anti-inflammatory drug).

In some embodiments, the outputs of one or more of the photodetectors 224, 226 and the temperature transducer 670 may be amplified by an amplifier 211. In some non-limiting embodiments, the amplifier 211 may be a comparator that receives analog light measurement signals from the photodetectors 224, 226 and output an analog light difference measurement signal indicative of the difference between the received analog light measurement signals. In some non-limiting embodiments, the amplifier 211 may be a transimpedance amplifier. However, in some alternative embodiments, a different amplifier may be used. In some embodiments, the outputs of one or more of the photodetectors 224, 226, the temperature transducer 670, and the amplifier 211 may be converted to a digital signal by an analog-to-digital converter (ADC) 213.

In some embodiments, one or more of the gain of the amplifier 211 and the drive current of the light source 108 may be initially set during a quality control process. In some embodiments, one or more of the gain of the amplifier 211 and the drive current of the light source 208 may be set to allow high dynamic range and to keep the modulated signal within the operational region. In some embodiments, any change (e.g., increase or decrease) to one or more of the drive current of the light source 208 and the gain of the amplifier 211 may change the modulated signal level accordingly.

In some embodiments, as illustrated in FIG. 2, the sensor 100 may include a substrate 216. In some embodiments, the substrate 216 may be a circuit board (e.g., a printed circuit board (PCB) or flexible PCB) on which circuit components (e.g., analog and/or digital circuit components) may be mounted or otherwise attached. However, in some alternative embodiments, the substrate 216 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 216. In other words, in some semiconductor substrate embodiments, a portion or all of the circuitry, which may include discrete circuit elements, an integrated circuit (e.g., an application specific integrated circuit (ASIC)) and/or other electronic components (e.g., a non-volatile memory), may be fabricated in the semiconductor substrate 216 with the remainder of the circuitry is secured to the semiconductor substrate 216 and/or a core (e.g., ferrite core) for an inductive element of the transceiver interface 103. In some embodiments, the semiconductor substrate 216 and/or a core may provide communication paths between the various secured components.

In some embodiments, one or more of the sensor housing 202, analyte indicator 206, indicator molecules 204, light source 208, photodetectors 224, 226, temperature transducer 670, substrate 216, and transceiver interface 103 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transceiver 101 may be as described in one or more of U.S. application Ser. Nos. 13/761,839, 13/937,871, and 13/650,016.

Figure 3:
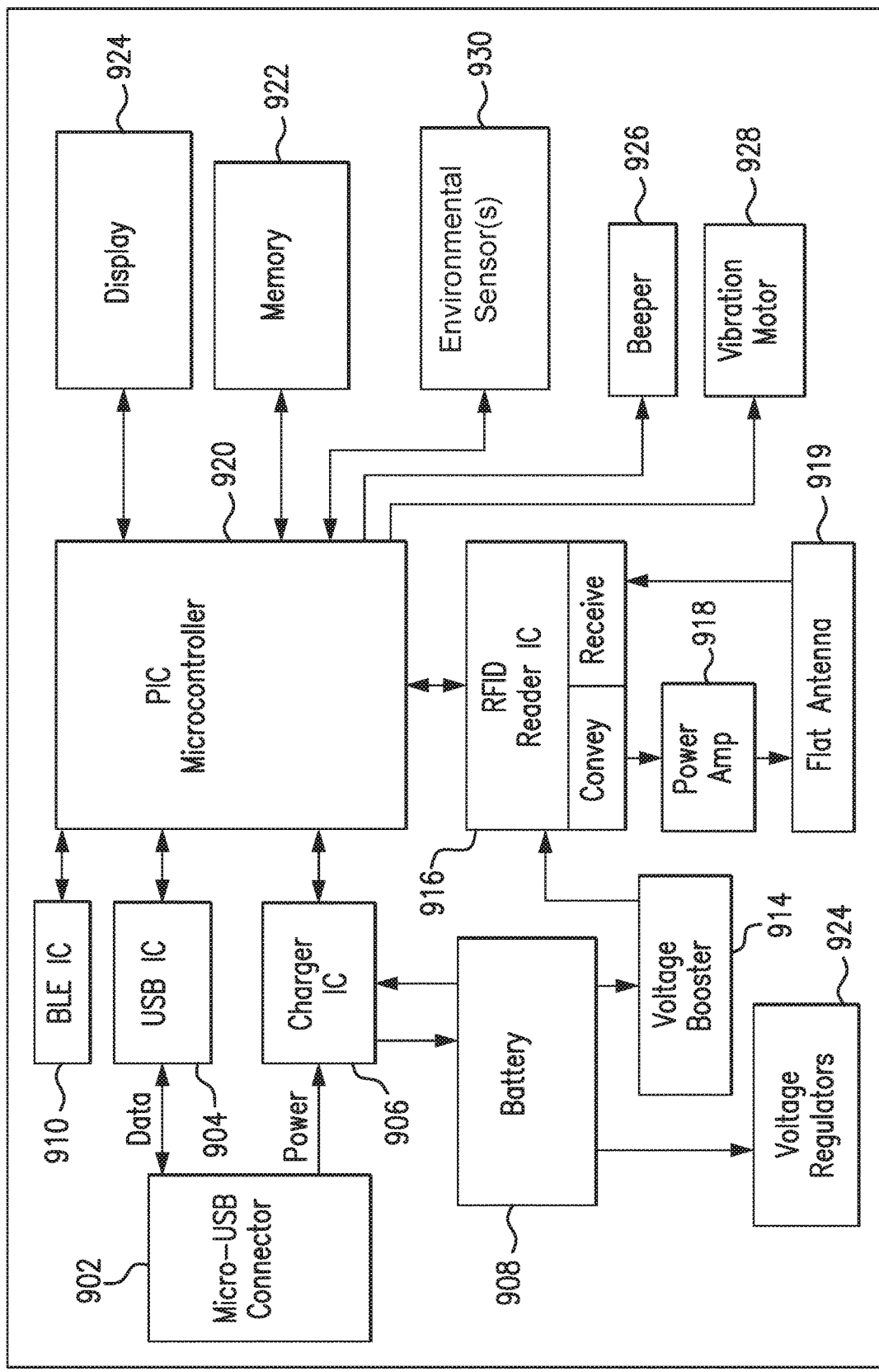
FIG. 3 is a schematic view illustrating a transceiver embodying aspects of the present invention.

FIG. 3 is a schematic view of the transceiver 101 according to a non-limiting embodiment. In some embodiments, as shown in FIG. 3, the transceiver 101 may have a connector 902, such as, for example and without limitation, a Micro-Universal Serial Bus (USB) connector. In some embodiments, the connector 902 may enable a wired connection to an external device, such as a personal computer (e.g., personal computer 109) or a display device 102 (e.g., a smartphone).

In some embodiments, the transceiver 101 may exchange data to and from the external device through the connector 902 and/or may receive power through the connector 902. The transceiver 101 may include a connector integrated circuit (IC) 904, such as, for example, a USB-IC, which may control transmission and receipt of data through the connector 902. The transceiver 101 may also include a charger IC 906, which may receive power via the connector 902 and charge or recharge a battery 908 (e.g., lithium-polymer battery).

In some embodiments, as shown in FIG. 3, the transceiver 101 may include one or more connectors in addition to (or as an alternative to) Micro-USB connector 902. For example, in one alternative embodiment, the transceiver 101 may include a spring-based connector (e.g., Pogo pin connector) in addition to (or as an alternative to) Micro-USB connector 902, and the transceiver 101 may use a connection established via the spring-based connector for wired communication to a personal computer (e.g., personal computer 109) or a display device 102 (e.g., a smartphone) and/or to receive power, which may be used, for example, to charge the battery 908.

In some embodiments, as shown in FIG. 3, the transceiver 101 may have a wireless communication IC 910, which enables wireless communication with an external device, such as, for example, one or more personal computers (e.g., personal computer 109) or one or more display devices 102 (e.g., a smartphone). In one non-limiting embodiment, the wireless communication IC 910 may employ one or more wireless communication standards to wirelessly transmit data. The wireless communication standard employed may be any suitable wireless communication standard, such as an ANT standard, a Bluetooth standard, or a Bluetooth Low Energy (BLE) standard (e.g., BLE 4.0). In some non-limiting embodiments, the wireless communication IC 910 may be configured to wirelessly transmit data at a frequency greater than 1 gigahertz (e.g., 2.4 or 5 GHz). In some embodiments, the wireless communication IC 910 may include an antenna (e.g., a Bluetooth antenna). In some non-limiting embodiments, the antenna of the wireless communication IC 910 may be entirely contained within the housing (e.g., housing 206 and 220) of the transceiver 101. However, this is not required, and, in alternative embodiments, all or a portion of the antenna of the wireless communication IC 910 may be external to the transceiver housing.

In some embodiments, as shown in FIG. 1B, the transceiver 101 may include a display interface 106, which may enable communication by the transceiver 101 with one or more display devices 102. In some embodiments, the display interface 106 may include the antenna of the wireless communication IC 910 and/or the connector 902 illustrated in FIG. 3. In some non-limiting embodiments, the display interface 106 may additionally include the wireless communication IC 910 and/or the connector IC 904 illustrated in FIG. 3.

In some embodiments, as shown in FIG. 3, the transceiver 101 may include voltage regulators 912 and/or a voltage booster 914. The battery 908 may supply power (via voltage booster 914) to radio-frequency identification (RFID) reader IC 916, which may use an inductive element 919 to convey information (e.g., commands) to the sensor 101 and receive information (e.g., measurement information) from the sensor 100. In some non-limiting embodiments, the sensor 100 and transceiver 101 may communicate using near field communication (NFC) (e.g., at a frequency of 13.56 MHz). In the illustrated embodiment, the inductive element 919 may be include a flat antenna. In some non-limiting embodiments, the antenna may be flexible. However, the inductive element 919 of the transceiver 101 may be in any configuration that permits adequate field strength to be achieved when brought within adequate physical proximity to an inductive element of the sensor 100. In some embodiments, the transceiver 101 may include a power amplifier 918 to amplify the signal to be conveyed by the inductive element 919 to the sensor 100.

In some embodiments, as shown in FIG. 3, the transceiver 101 may include a peripheral interface controller (PIC) microcontroller 920 and memory 922 (e.g., Flash memory), which may be non-volatile and/or capable of being electronically erased and/or rewritten. The PIC microcontroller 920 may control the overall operation of the transceiver 101. For example, the PIC microcontroller 920 may control the connector IC 904 or wireless communication IC 910 to transmit data via wired or wireless communication and/or control the RFID reader IC 916 to convey data via the inductive element 919. The PIC microcontroller 920 may also control processing of data received via the inductive element 919, connector 902, or wireless communication IC 910.

In some embodiments, as shown in FIG. 1B, the transceiver 101 may include a sensor interface 104, which may enable communication between the transceiver 101 and sensor 100. In some embodiments, the sensor interface 104 may include the inductive element 919 illustrated in FIG. 3. In some non-limiting embodiments, the sensor interface 104 may additionally include the RFID reader IC 916 and/or the power amplifier 918 illustrated in FIG. 3. However, in some alternative embodiments where there exists a wired connection between the sensor 100 and the transceiver 101 (e.g., transcutaneous embodiments), the sensor interface 104 may include the wired connection.

In some embodiments, as shown in FIG. 3, the transceiver 101 may include a display 924 (e.g., liquid crystal display and/or one or more light emitting diodes), which PIC microcontroller 920 may control to display data (e.g., analyte levels). In some embodiments, the transceiver 101 may include a speaker 926 (e.g., a beeper) and/or vibration motor 928, which may be activated, for example, in the event that an alarm condition (e.g., detection of a hypoglycemic or hyperglycemic condition) is met.

In some embodiments, as shown in FIG. 3, the transceiver 101 may include one or more environmental sensors 930. In some embodiments, the environmental sensors 930 may include one or more the posture sensors 110, pressure sensors 111, shock sensors 113, and temperature sensors 105 illustrated in FIG. 1B.

In some embodiments, the transceiver 101 may be a body-worn transceiver that is a rechargeable, external device worn over the sensor implantation or insertion site. The transceiver 101 may supply power to the proximate sensor 100, calculate analyte levels from data received from the sensor 100, and/or transmit the calculated analyte levels to a display device 102 (see FIGS. 1A and 1B). Power may be supplied to the sensor 100 through an inductive link (e.g., an inductive link of 13.56 MHz). In some embodiments, the transceiver 101 may be placed using an adhesive patch or a specially designed strap or belt. The external transceiver 101 may read measured analyte data from a subcutaneous sensor 100 (e.g., up to a depth of 2 cm or more). The transceiver 101 may periodically (e.g., every 2, 5, or 10 minutes) read sensor data and calculate an analyte levels and an analyte levels trend. From this information, the transceiver 101 may also determine if an alert and/or alarm condition exists, which may be signaled to the user (e.g., through vibration by vibration motor 928 and/or an LED of the transceiver's display 924 and/or a display 108 of a display device 102). The information from the transceiver 101 (e.g., calculated analyte levels, calculated analyte levels trends, alerts, alarms, and/or notifications) may be transmitted to a display device 102 (e.g., via Bluetooth Low Energy with Advanced Encryption Standard (AES)-Counter CBC-MAC (CCM) encryption) for display by a mobile medical application (MMA) being executed by the display device 102. In some non-limiting embodiments, the MMA may provide alarms, alerts, and/or notifications in addition to any alerts, alarms, and/or notifications received from the transceiver 101. In one embodiment, the MMA may be configured to provide push notifications.

In some embodiments, the transceiver 101 of the analyte monitoring system 120 may receive one or more sensor measurements indicative of an amount, level, or concentration of an analyte in a first medium (e.g., interstitial fluid ("ISF")) in proximity to the analyte sensor 100. In some embodiments, the transceiver 101 may receive the sensor measurements conveyed by the sensor 100 periodically (e.g., every 1, 2, 5, 10, 15, or 20 minutes). In some embodiments, the one or more sensor measurements may include, for example and without limitation, one or more of (i) one or more measurements indicative of an amount of emission light from indicator molecules of the sensor elements 112 (e.g., as measured by one or more photodetectors of the sensor elements 112), (ii) one or more measurements indicative of an amount of reference light (e.g., as measured by one or more photodetector of the sensor elements 112), and (iii) one or more temperature measurements (e.g., as measured by one or more temperature transducers 670 of the sensor elements 112). In some embodiments, the transceiver 101 may use the received sensor measurements to calculate a first medium analyte level (e.g., an ISF analyte level).

In some embodiments, the transceiver 101 may use the calculated first medium analyte level and at least one or more previously calculated first medium analyte levels to calculate a rate of change of the first medium analyte level ("M1_ROC"). In some non-limiting embodiments, to calculate M1_ROC, the transceiver 101 may use just the calculated first medium analyte level and the most recent previously calculated first medium analyte level and determine M1_ROC as the difference between the calculated first medium analyte level and most recent previously calculated first medium analyte level divided by the time difference between a time stamp for the calculated first medium analyte level and a time stamp for the most recent previously calculated first medium analyte level. In some alternative embodiments, to calculate M1_ROC, the transceiver 101 may use the calculated first medium analyte level and a plurality of the most recent previously calculated first medium analyte levels. In some non-limiting embodiments, the plurality of the most recent previously calculated first medium analyte levels may be, for example and without limitation, the previous two calculated first medium analyte levels, the previous 20 calculated first medium analyte levels, or any number of previously calculated first medium analyte levels in between (e.g., the previous 5 calculated first medium analyte levels). In other alternative embodiments, to calculate M1_ROC, the transceiver 101 may use the calculated first medium analyte level and the previously calculated first medium analyte levels that were calculated during a time period. In some non-limiting embodiments, the time period may be, for example and without limitation, the last one minute, the last 60 minutes, or any amount of time in between (e.g., the last 25 minutes). In some embodiments where the transceiver 101 uses the calculated first medium analyte level and more than one previously calculated first medium analyte levels to calculate M1_ROC, the transceiver 101 may use, for example, linear or non-linear regression to calculate M1_ROC.

In some embodiments, the transceiver 101 may convert the calculated first medium analyte level into a second medium analyte level (e.g., a blood analyte level) by performing a lag compensation, which compensates for the time lag between a second medium analyte level and an first medium analyte level (e.g., the time lag between a blood analyte level and an ISF analyte level). In some embodiments, the transceiver 101 may calculate the second medium analyte level using at least the calculated first medium analyte level and the calculated M1_ROC. In some non-limiting embodiments, the transceiver 101 may calculate the second medium analyte level as $M1\_ROC/p_2+(1+p_3/p_2)*M1\_analyte$, where $p_2$ is analyte diffusion rate, $p_3$ is the analyte consumption rate, and M1_analyte is the calculated first medium analyte level.

In some embodiments, one or more environmental factors may affect the lag between the second medium analyte level and the first medium analyte level. For example and without limitation, one or more environmental factors may affect (i) the user's blood flow in proximity to the sensor 100 and/or (ii) the transfer of the analyte from the second medium (e.g., blood) to the first medium (e.g., interstitial fluid) in proximity to the sensor 100. The environmental factors may include, for example and without limitation, a user's posture, pressure on the sensing region, shock to the sensing region, and temperature changes in the sensing region. In some embodiments, the analyte monitoring system 120 may use one or more environmental measurements indicative of one or more environmental factors to improve the calculation of second medium analyte levels. In some non-limiting embodiments, the analyte monitoring system 120 may use one or more environmental measurements indicative of one or more environmental factors to improve the conversion of a first analyte medium level to second medium analyte level.

In some embodiments, the transceiver 101 may use one or more sensor measurements received from the analyte sensor 100 and one or more environmental measurements (e.g., one or more environmental measurements generated by the one or more environmental sensors 930) to calculate a second medium analyte level. In some non-limiting embodiments, the transceiver 101 may adjust a conversion function used to calculate a second medium analyte level based on one or more environmental measurements generated by the one or more environmental sensors 930. In some non-limiting embodiments, the transceiver 101 may adjust the conversion function by adjusting one or more parameters (e.g., one or more of the analyte diffusion rate and analyte consumption rate parameters) of the conversion function. In some non-limiting embodiments, the transceiver 101 may adjust one or more of $p_2$ and $p_3$ (or one or more of $1/p_2$ and $p_3/p_2$) in the conversion function that calculates a second medium analyte level as $M1\_ROC/p_2+(1+p_3/p_2)*M1\_analyte$. In some alternative embodiments, the transceiver 101 may select one of a plurality of conversion functions based on one or more environmental measurements generated by the one or more environmental sensors 930.

In some embodiments, a user's posture (e.g., whether the user is lying down, sitting up, or standing) may affect (i) the user's blood flow in proximity to the sensor 100 and/or (ii) the transfer of the analyte from the second medium (e.g., blood) to the first medium (e.g., interstitial fluid) in proximity to the sensor 100. In some embodiments, the transceiver 101 may calculate the second medium analyte level (e.g., blood analyte level) using at least one or more sensor measurements received from the analyte sensor 100 and one or more posture measurements generated by the posture sensor 110. In some non-limiting embodiments, the transceiver 101 may calculate a posture of the user of transceiver 101 using the one or more posture measurements generated by the posture sensor 110. In some non-limiting embodiments, the transceiver 101 may calculate the second medium analyte level using at least one or more sensor measurements received from the analyte sensor 100 and the calculated posture. In some non-limiting embodiments, the transceiver 101 may adjust one or more parameters of the conversion function (e.g., the analyte diffusion rate) based on at least the calculated posture and use the adjusted conversion function and the one or more sensor measurements received from the analyte sensor 100 to calculate the second medium analyte level. In some non-limiting alternative embodiments, the transceiver 101 may select one of a plurality of conversion functions based on the calculated posture and use the selected conversion function and the one or more sensor measurements received from the analyte sensor 100 to calculate the second medium analyte level.

In some non-limiting embodiments, the transceiver 101 may additionally or alternatively change the sampling frequency of one or more sensors (e.g., the frequency at which one or more posture sensors 110, one or more pressure sensors 111, one or more shock sensors 113, and/or one or more temperature sensors 105 generate measurements) based on the calculated posture. In some non-limiting embodiments, based on the calculated posture, the transceiver 101 may additionally or alternatively cause one or more of the transceiver 101 and the display device 102 to display one or more icons indicative of environmental events (e.g., an icon indicative of a posture of the user of the transceiver 101).

In some embodiments, pressure on the user's body in proximity to the sensor 100 (e.g., whether the user is lying on the sensor 100 or wearing tight clothing around the sensor 100) may affect (i) the user's blood flow in proximity to the sensor 100 and/or (ii) the transfer of the analyte from the second medium (e.g., blood) to the first medium (e.g., interstitial fluid) in proximity to the sensor 100. In some embodiments, the transceiver 101 may calculate the second medium analyte level (e.g., blood analyte level) using at least one or more sensor measurements received from the analyte sensor 100 and one or more pressure measurements generated by the pressure sensor 111. In some non-limiting embodiments, the transceiver 101 may adjust one or more parameters of the conversion function (e.g., the analyte diffusion rate) based on at least the one or more pressure measurements and use the adjusted conversion function and the one or more sensor measurements received from the analyte sensor 100 to calculate the second medium analyte level. In some non-limiting alternative embodiments, the transceiver 101 may select one of a plurality of conversion functions based on the one or more pressure measurements and use the selected conversion function and the one or more sensor measurements received from the analyte sensor 100 to calculate the second medium analyte level.

In some non-limiting embodiments, the transceiver 101 may additionally or alternatively change the sampling frequency of one or more sensors (e.g., the frequency at which one or more posture sensors 110, one or more pressure sensors 111, one or more shock sensors 113, and/or one or more temperature sensors 105 generate measurements) based on the one or more pressure measurements. In some non-limiting embodiments, based on the one or more pressure measurements, the transceiver 101 may additionally or alternatively cause one or more of the transceiver 101 and the display device 102 to display one or more icons indicative of environmental events (e.g., an icon indicative of pressure on the user's body in proximity to the sensor 100).

In some embodiments, bruising and/or blood in proximity to the sensor 100 (e.g., due to shocks or impacts to the user's body) may affect (i) the user's blood flow in proximity to the sensor 100 and/or (ii) the transfer of the analyte from the second medium (e.g., blood) to the first medium (e.g., interstitial fluid) in proximity to the sensor 100. In some embodiments, the transceiver 101 may calculate the second medium analyte level (e.g., blood analyte level) using at least one or more sensor measurements received from the analyte sensor 100 and one or more acceleration measurements generated by the shock sensor 113. In some non-limiting embodiments, the transceiver 101 may determine whether a shock to the transceiver 101 has occurred using the one or more acceleration measurements generated by the shock sensor 113. In some non-limiting embodiments, the transceiver 101 may calculate the second medium analyte level using at least one or more sensor measurements received from the analyte sensor 100 and the determination of whether a shock to the transceiver 101 has occurred. In some non-limiting embodiments, the transceiver 101 may adjust one or more parameters of the conversion function (e.g., the analyte diffusion rate) based on at least the shock determination and use the adjusted conversion function and the one or more sensor measurements received from the analyte sensor 100 to calculate the second medium analyte level. In some non-limiting alternative embodiments, the transceiver 101 may select one of a plurality of conversion functions based on the shock determination and use the selected conversion function and the one or more sensor measurements received from the analyte sensor 100 to calculate the second medium analyte level.

In some non-limiting embodiments, the transceiver 101 may additionally or alternatively change the sampling frequency of one or more sensors (e.g., the frequency at which one or more posture sensors 110, one or more pressure sensors 111, one or more shock sensors 113, and/or one or more temperature sensors 105 generate measurements) based on the shock determination. In some non-limiting embodiments, based on the shock determination, the transceiver 101 may additionally or alternatively cause one or more of the transceiver 101 and the display device 102 to display one or more icons indicative of environmental events (e.g., an icon indicative of a shock or impact to the user's body).

In some non-limiting embodiments, the transceiver 101 may additionally or alternatively adjust one or more of the received sensor measurements (e.g., one or more temperature measurements of the received sensor measurements). For example and without limitation, the transceiver 101 may adjust one or more temperature measurements of the received sensor measurements. In some embodiments, the temperature measurements may reflect the temperature inside the sensor 100 (e.g., the temperature of the substrate 216 as measured by the temperature transducer 670 of the sensor 100) as opposed to the temperature of the analyte indicator 206, which may be on the exterior of the sensor 100. In some embodiments, the transceiver 101 may adjust one or more temperature measurements because, as shown in FIG. 4, the temperature inside the sensor 100 may lag behind the temperature of the analyte indicator 206.

Figure 4:
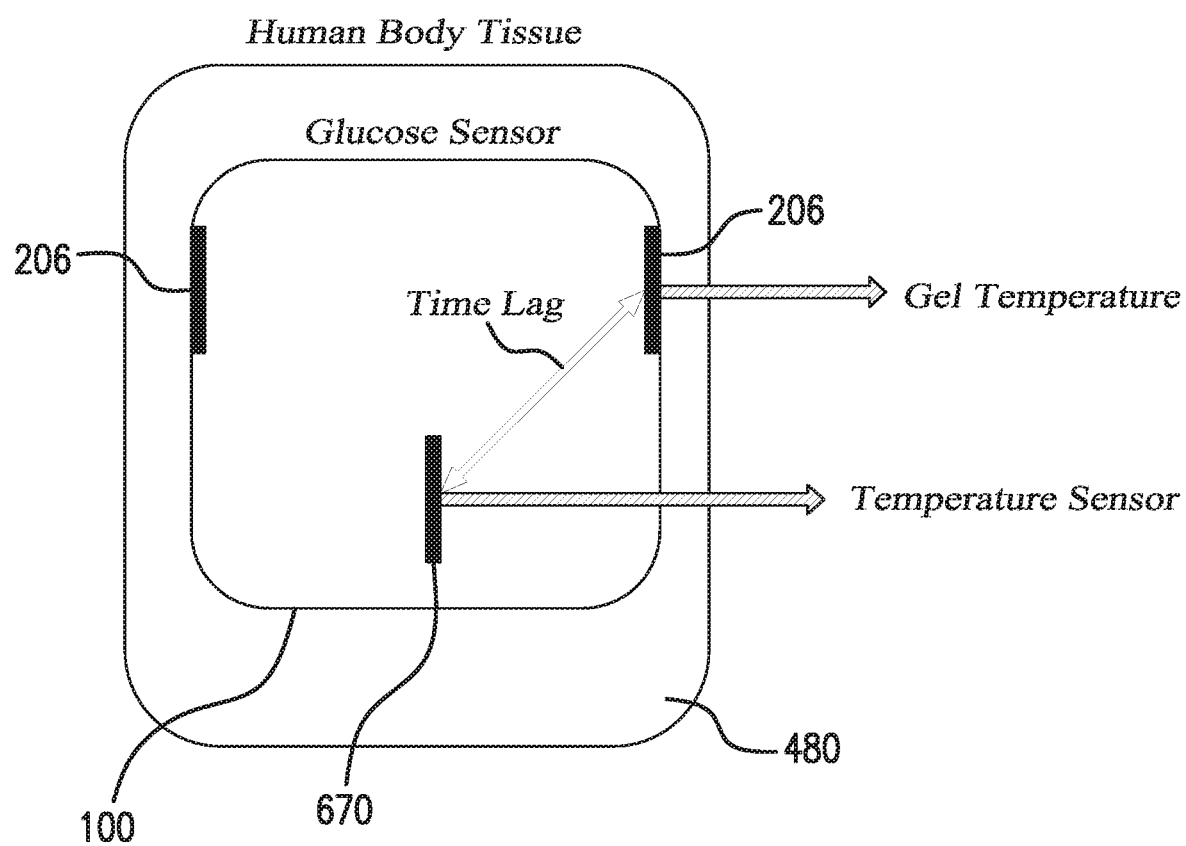
FIG. 4 is a schematic view illustrating the time lag between a temperature of an analyte indicator on or in the exterior surface of an analyte sensor and a temperature inside the analyte sensor embodying aspects of the present invention.

In some embodiments, as shown in FIG. 4, the analyte indicator 206 of an implanted sensor 100 may be in contact with subcutaneous tissue 480, and interstitial fluid of the subcutaneous tissue 480 may permeate the analyte indicator 206. Accordingly, the temperature of the analyte indicator 206 may correspond to the temperature of the subcutaneous tissue 480 in proximity to the sensor 100. In some non-limiting embodiments, the time lag between the temperature of the analyte indicator 206 and the temperature inside the sensor 100 (as measured by the temperature transducer 670) may be due to the thermal properties (e.g., thermal conductivity) of the materials of the sensor body. As a result, when the temperature of the analyte indicator 206 changes, there may be a delay before the change is reflected in the temperature measurements taken by one or more temperature transducers 670 of the sensor elements 112 of the analyte sensor 100. In some embodiments, the analyte monitoring system 120 (e.g., the transceiver 101 of the system 120) may use one or more temperature measurements received from the sensor 100 in the calculation of analyte levels (e.g., analyte concentrations). Thus, the lag between the measured temperature and the temperature of the analyte indicator 206 may impact negatively the accuracy of the calculated analyte levels.

In some embodiments, the transceiver 101 may adjust one or more temperature measurements received from the analyte sensor 100 to compensate for the time lag between the measured temperature and the temperature of the analyte indicator 206. In some embodiments, the transceiver 101 may adjust one or more received temperature measurements to be estimates of the temperature of the analyte indicator 206 instead of measurements of the temperature inside the sensor 100. In some non-limiting embodiments, the transceiver 101 may use the adjusted temperature measurements to calculate one or more analyte levels (e.g., one or more first medium analyte levels and/or one or more second medium analyt levels).

Figure 5A:
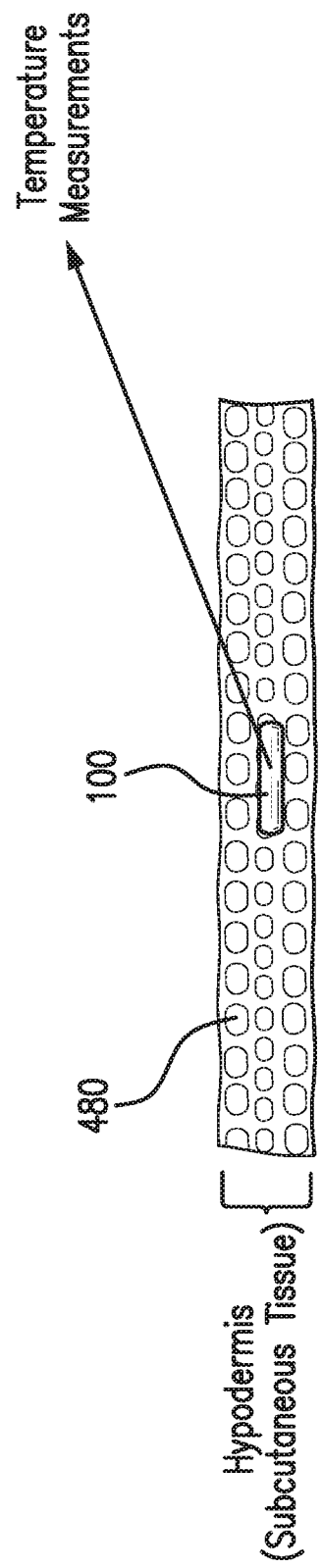
FIGS. 5A and 5B are schematic views illustrating single compartment models of the lag between the temperature of an analyte indicator of an analyte sensor and the temperature inside the analyte sensor embodying aspects of the present invention.
Figure 5B:
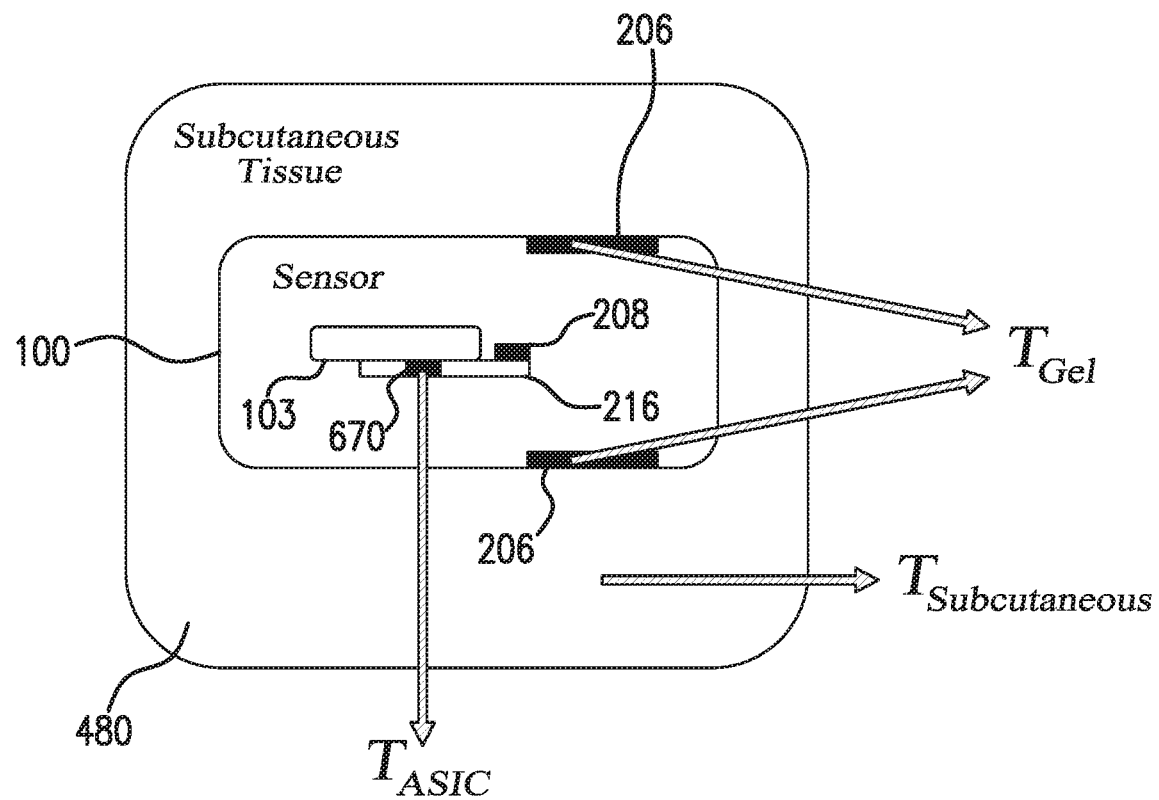

In some non-limiting embodiments, the transceiver 101 may use a single compartment model to estimate the temperature of the analyte indicator 206. FIGS. 5A and 5B illustrate examples of single compartment models for estimating the temperature of the interstitial fluid in the subcutaneous tissue 480 in proximity to the analyte indicator 206. With the single compartment model, $dT_S/dt = T_{Sub}/\tau - T_S/\tau$, where $T_{Sub}$ is the temperature of the subcutaneous tissue 480, $T_S$ is the temperature of the sensor 100, $\tau$ is the rate constant between the subcutaneous tissue 480 and the sensor 100, and $dT_S/dt$ is the derivative of the temperature of the sensor 100 with respect to time. Based on this equation, $T_{Sub} = \tau * dT_S/dt + T_S$. In some non-limiting embodiments, $\tau$ may range, for example and without limitation, from milliseconds to minutes for electronics encasement materials of the sensor 100.

In some embodiments, the transceiver 101 may receive a temperature measurement from the sensor 100. In some embodiments, the transceiver 101 may calculate a rate of change of the temperature of the sensor 100 ($T_S\_ROC$) using at least the received temperature measurement and one or more previous temperature measurements. In some non-limiting embodiments, to calculate $T_S\_ROC$, the transceiver 101 may use just the received temperature measurement and the most recent previously received temperature measurement and determine $T_S\_ROC$ as the difference between the received temperature measurement and most recent previously received temperature measurement divided by the time difference between a time stamp associated with the received temperature measurement and a time stamp associated with the most recent previously received temperature measurement. In some alternative embodiments, to calculate $T_S\_ROC$, the transceiver 101 may use the received temperature measurement and a plurality of the most recent previously received temperature measurements. In some non-limiting embodiments, the plurality of the most recent previously received temperature measurements may be, for example and without limitation, the previous two received temperature measurements, the previous 20 received temperature measurement, or any number of previously calculated received temperature measurements in between (e.g., the previous 5 received temperature measurements). In other alternative embodiments, to calculate $T_S\_ROC$, the transceiver 101 may use the received temperature measurement and the previous temperature measurements that were received during a time period. In some non-limiting embodiments, the time period may be, for example and without limitation, the last one minute, the last 60 minutes, or any amount of time in between (e.g., the last 25 minutes). In some embodiments where the transceiver 101 uses the received temperature measurement and more than one previously received temperature measurements to calculate $T_S\_ROC$, the transceiver 101 may use, for example, linear or non-linear regression to calculate $T_S\_ROC$.

In some non-limiting embodiments, the transceiver 101 may calculate an estimated temperature of the analyte indicator 206 using at least the received temperature measurement and the calculated rate of change of the temperature of the sensor 100 ($T_S\_ROC$). In some embodiments, because interstitial fluid of the subcutaneous tissue 480 permeates the analyte indicator 206, the transceiver 101 may treat the temperature of the analyte indicator 206 as equal to the temperature of the subcutaneous tissue 480 ($T_{Sub}$) and calculate the estimated temperature of the analyte indicator 206 using the equation above for the temperature of the subcutaneous tissue 480 ($T_{Sub}$). In some embodiments, the transceiver 101 may use the received temperature measurement and the calculated rate of change of the temperature of the sensor 100 ($T_S\_ROC$) as the temperature of the sensor 100 ($T_S$) and the derivative of the temperature of the sensor 100 with respect to time ($dT_S/dt$), respectively, in the equation above for the temperature of the subcutaneous tissue 480 ($T_{Sub}$). In some embodiments, the transceiver 101 may use the estimated temperature of the analyte indicator 206 (instead of the received temperature measurement) to calculate the second medium analyte level (e.g., the blood analyte level). In some non-limiting embodiments, the transceiver 101 may use the estimated temperature of the analyte indicator 206 (instead of the received temperature measurement) to calculate the first medium analyte level (e.g., the ISF analyte level), which may be used to calculate the second medium analyte level.

Figure 6:
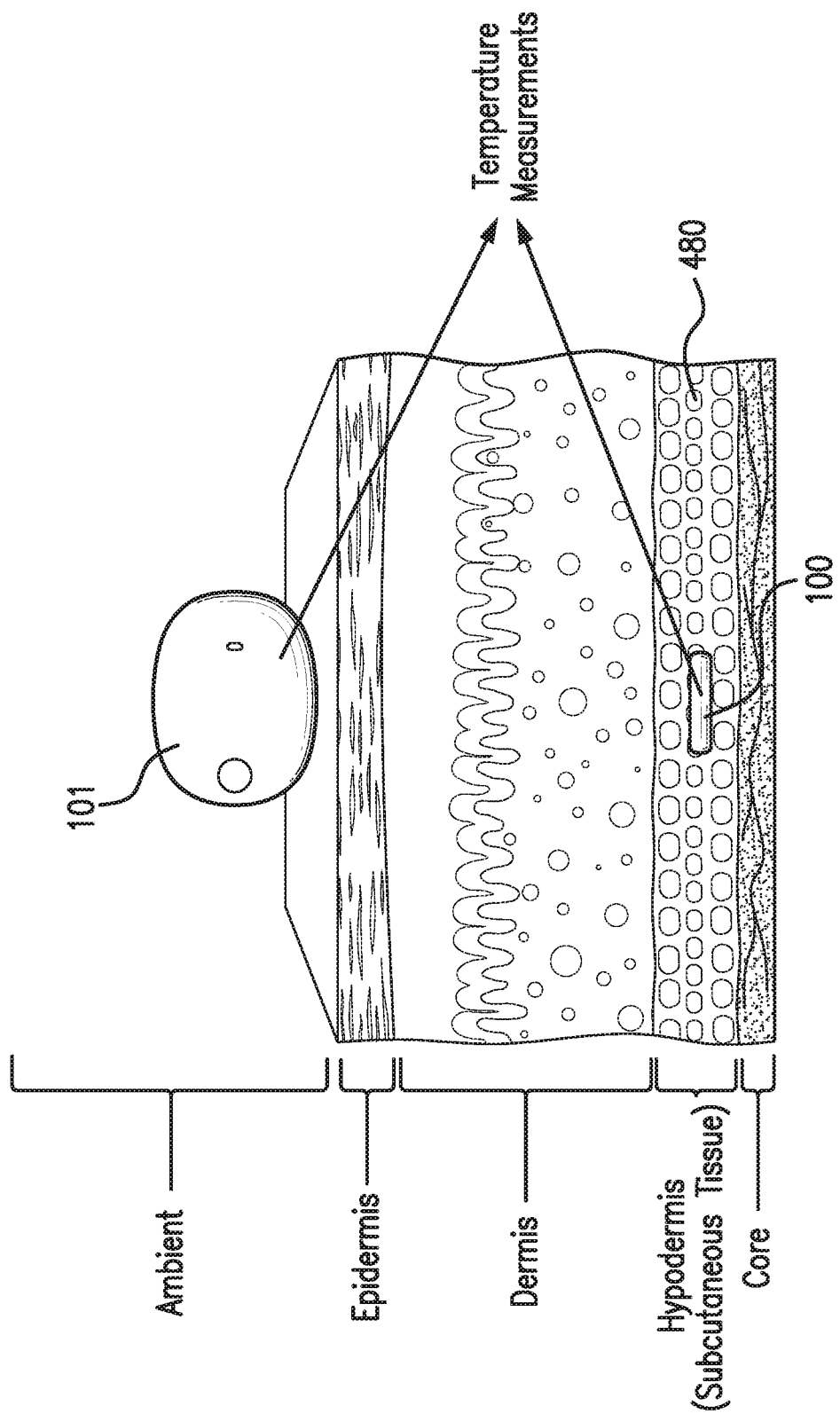
FIG. 6 is schematic view illustrating a multi-compartment model of the lag between the temperature of an analyte indicator of an analyte sensor and the temperature inside the analyte sensor embodying aspects of the present invention.

In some non-limiting alternative embodiments, the transceiver 101 may use a multi-compartment model to estimate the temperature of the analyte indicator 206. FIG. 6 illustrates an example of a multi-compartment model for estimating the temperature of the interstitial fluid in the subcutaneous tissue 480 in proximity to the analyte indicator 206. In some embodiments, as shown in FIG. 6, the sensor 100 may be implanted in the hypodermis or subcutaneous tissue 480, which is above the core and below the dermis and epidermis.

In some embodiments, the one or more temperature sensors 105 of the transceiver 101 may detect temperature changes before the one or more temperature transducers 670 of the sensor elements 112 of the analyte sensor 100. For example and without limitation, if a user gets into an ice bath or a hot tub, the one or more temperature sensors 105 of the transceiver 101 may detect the resultant temperature change before the one or more temperature transducers 670 of the sensor elements 112 of the analyte sensor 100. In some embodiments, the transceiver 101 may use one or more temperature measurements generated by the one or more temperature sensors 105 of the transceiver 101 to predict changes in the interstitial fluid in the subcutaneous tissue 480 in proximity to the sensor 100. In some embodiments, the transceiver 101 may use the one or more temperature measurements generated by the one or more temperature sensors 105 of the transceiver 101 to adjust one or more temperature measurements generated by the one or more temperature transducers 670 of the sensor elements 112 of the analyte sensor 100. In some embodiments, the adjustments may account for the lag between (i) temperature changes to the interstitial fluid of the subcutaneous tissue 480 that permeates the analyte indicator 206 of the sensor 100 and (ii) temperature changes in the sensor 100. In some embodiments, the adjusted temperature measurements may reflect the temperature of the analyte indicator 206 of the sensor 100 more accurately than the unadjusted temperature measurements. In some embodiments, the transceiver 101 may use one or more adjusted temperature measurements (instead of the original temperature measurements conveyed by the sensor 100) to calculate the second medium analyte level (e.g., the blood analyte level). In some non-limiting embodiments, the transceiver 101 may use one or more adjusted temperature measurements (instead of the original temperature measurements conveyed by the sensor 100) to calculate the first medium analyte level (e.g., the ISF analyte level), which may be used to calculate the second medium analyte level.

In some embodiments, the transceiver 101 may receive a temperature measurement conveyed by the sensor 100. In some embodiments, the transceiver 101 may calculate a rate of change of the temperature of the sensor 100 ($T_S\_ROC$) using at least the received temperature measurement and one or more temperature measurements previously received from the sensor 100. In some embodiments, the transceiver 101 may calculate a rate of change of the temperature of the transceiver 101 ($T_T\_ROC$) using at least a temperature measurement generated by a temperature sensor 105 (e.g., of the transceiver 101) and one or more temperature measurements previously generated by the temperature sensor 105. In some non-limiting embodiments, $T_T\_ROC$ may be calculated in a manner similar to any of the manners that may be used to calculate $T_S\_ROC$. In some non-limiting embodiments, the transceiver 101 may calculate an estimated temperature of the analyte indicator 206 using at least the temperature measurement received from the sensor 100, the calculated rate of change of the temperature of the sensor 100 ($T_S\_ROC$), the temperature measurement generated by a temperature sensor 105, and the calculated rate of change of the temperature of the transceiver 101 ($T_T\_ROC$). In some embodiments, the transceiver 101 may use the estimated temperature of the analyte indicator 206 (instead of the temperature measurement received from the sensor 100) to calculate the second medium analyte level (e.g., the blood analyte level). In some non-limiting embodiments, the transceiver 101 may use the estimated temperature of the analyte indicator 206 (instead of the temperature measurement received from the sensor 100) to calculate the first medium analyte level (e.g., the ISF analyte level), which may be used to calculate the second medium analyte level.

In some non-limiting embodiments, as described above, a single compensation model may be used to compensate for the lag between one or more measured temperatures (e.g., the temperature of the sensor 100 as measured by a temperature transducer 670 and/or the temperature of the transceiver 101 as measured by a temperature sensor 105) and the temperature of the temperature of analyte indicator 206. In some embodiments, a single compensation model may compensate for one medium in the lag compensation model. In some single compensation model embodiments, the temperature may be compensated with single variable temperature estimations. In some non-limiting embodiments, the single variable may be τ (i.e., the rate constant between the subcutaneous tissue 480 and the sensor 100). In some non-limiting alternative embodiments, a multi-compensation model may be used to compensate for the lag between one or more measured temperatures (e.g., the temperature of the sensor 100 as measured by a temperature transducer 670 and/or the temperature of the transceiver 101 as measured by a temperature sensor 105) and the temperature of the temperature of analyte indicator 206. In some multi-compensation model embodiments, the temperature may be compensated with multivariable variable temperature estimations. In some embodiments, the multiple variables may be different rate constants for different media through which the compensation is being applied.

In some non-limiting embodiments, the transceiver 101 may additionally or alternatively change the sampling frequency of one or more sensors (e.g., the frequency at which one or more posture sensors 110, one or more pressure sensors 111, one or more shock sensors 113, and/or one or more temperature sensors 105 generate measurements) based on one or more temperature measurements generated by the one or more temperature sensors 105 of the transceiver 101 (e.g., based on a rate of temperature change indicated by the temperature measurements). In some non-limiting embodiments, based on one or more temperature measurements generated by the one or more temperature sensors 105 of the transceiver 101, the transceiver 101 may additionally or alternatively cause one or more of the transceiver 101 and the display device 102 to display one or more icons indicative of environmental events (e.g., an icon indicative of a temperature change if the temperature measurements indicate a rate of temperature change greater than a threshold).

In some embodiments, the transceiver 101 may receive temperature measurements more frequently than the transceiver 101 receives analyte measurements (e.g., light measurements). In some non-limiting embodiments, the more frequent temperature measurements may enable the transceiver 101 to calculate more accurate rates of temperature change (e.g., $T_S\_ROC$ and $T_T\_ROC$). In some non-limiting embodiments, the transceiver 101 may convey analyte measurement and temperature measurement commands to the sensor 100. In response to an analyte measurement command, the sensor 100 may convey sensor data including one or more light measurements and one or more temperature measurements to the transceiver 101. In response to a temperature measurement commands, the sensor 100 may convey sensor data including one or more temperature measurements (and no light measurements) to the transceiver 101. In some non-limiting embodiments, the sensor 100 may not activate the light source 208 during execution of a temperature measurement command.

In some non-limiting embodiments, the transceiver 101 may change the sampling frequency of one or more temperature sensors (e.g., the sample frequency of one or more temperature transducers 670 and/or one or more temperature sensors 105). In some non-limiting embodiments, the transceiver 101 may change the sampling frequency of one or more temperature sensors, for example and without limitation, when analyte level is rising or falling at a fast rate and/or when the analyte level is in or approaching a hypo- or hyperglycemic range. In some non-limiting embodiments, the estimation of the temperature of the analyte indicator 206 may be applied to different temperature sampling rates.

Figure 7:
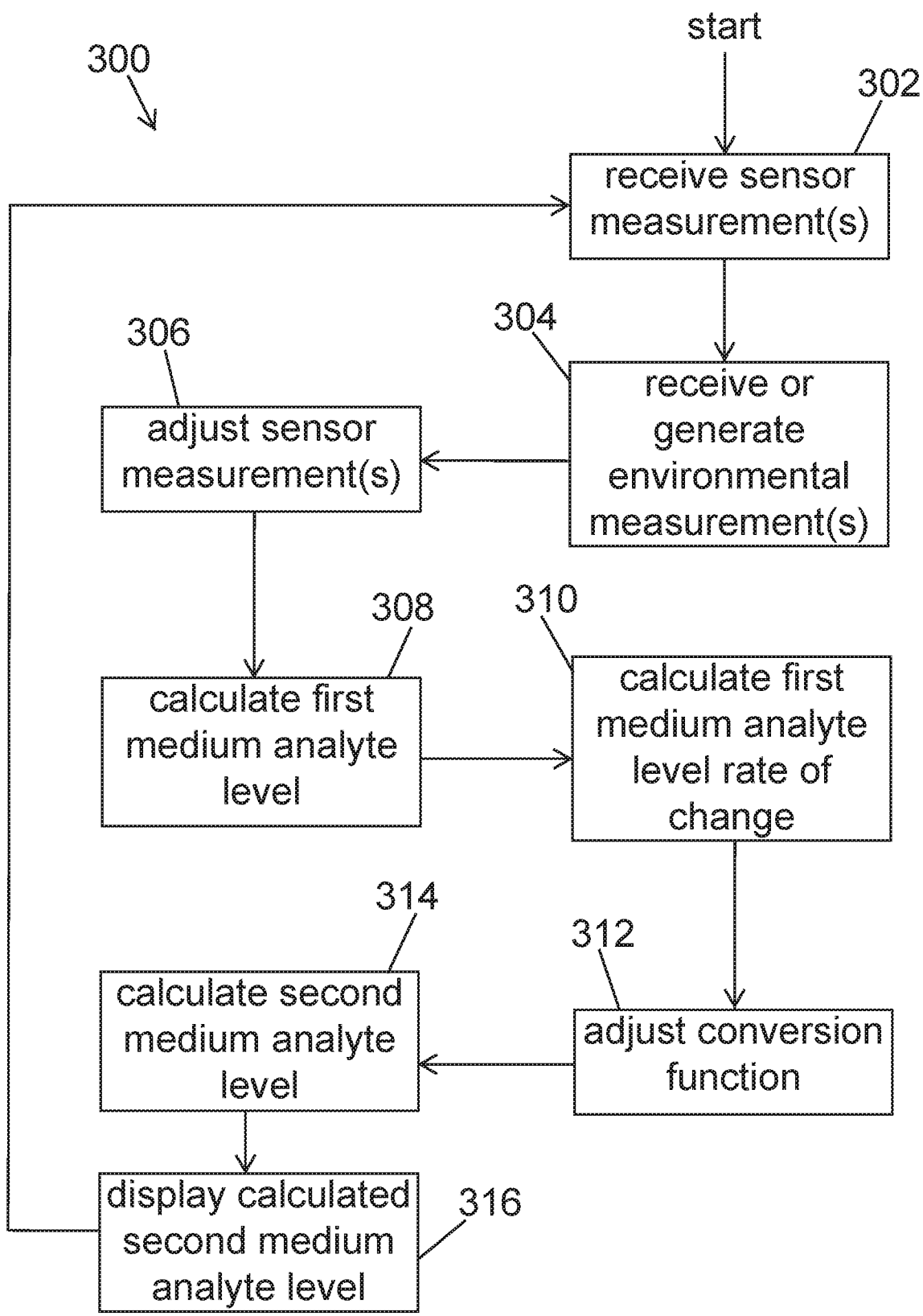
FIG. 7 is a flow chart illustrating an analyte level calculation process embodying aspects of the present invention.

FIG. 7 is a flow chart illustrating a process 300 for calculating second medium analyte levels (e.g., blood analyte levels). In some embodiments, one or more steps of the process 300 may be performed by an analyte monitoring system, such as, for example, the analyte monitoring system 120. In some embodiments, one or more steps of the process 300 may be performed by a transceiver, such as, for example, the transceiver 101. In some non-limiting embodiments, one or more steps of the process 300 may be performed by a processor, such as, for example, the PIC microcontroller 920 of the transceiver 101.

In some embodiments, the process 300 may include a step 302 in which the transceiver 101 receives one or more sensor measurements conveyed by the sensor 100. In some non-limiting embodiments, the one or more sensor measurements may include, for example and without limitation, one or more light measurements and/or one or more temperature measurements. In some embodiments, the transceiver 101 may receive the one or more sensor measurements after conveying a command (e.g., a measurement command or a read sensor data command) to the sensor 100. However, this is not required, and, in some alternative embodiments, the sensor 100 may control when one or more sensor measurements are conveyed to the transceiver 101, or the sensor 100 may continuously convey sensor measurements to the transceiver 101. In some non-limiting embodiments, the transceiver 101 may receive one or more sensor measurements periodically (e.g., every 1, 2, 5, 10, or 15 minutes).

In some embodiments, the transceiver 101 may receive the one or more sensor measurements using the sensor interface device 104 of the transceiver 101. In some non-limiting embodiments, the transceiver 101 may receive the one or more sensor measurements wirelessly. For example and without limitation, in some non-limiting embodiments, the transceiver 101 may receive the one or more sensor measurements by detecting modulations in an electromagnetic wave generated by the sensor 100, e.g., by detecting modulations in the current flowing through the inductive element 919 of the transceiver 101. However, this is not required, and, in some alternative embodiments, the transceiver 101 may receive the sensor data via a wired connection to the sensor 100.

In some embodiments, the one or more sensor measurements may be associated with a time stamp. In some non-limiting embodiments, the transceiver 101 may receive the time stamp from the sensor 100. In some non-limiting embodiments, the received one or more sensor measurements may include the time stamp. In some embodiments, the time stamp may reflect the time at which the one or more sensor measurements were taken. However, it is not required that the transceiver 101 receive the time stamp from the sensor 100. For example, in some alternative embodiments, the transceiver 101 may assign the time stamp to the one or more sensor measurements after receiving the one or more sensor measurements. In these embodiments, the time stamp may reflect when the transceiver 101 received the one or more sensor measurements.

In some embodiments, the process 300 may include a step 304 in which the transceiver 101 receives or generates one or more environmental measurements. In some embodiments, the one or more environmental measurements may include one or more one or more posture measurements indicative of the posture of a user of the transceiver 101, one or more pressure measurements indicative of pressure on the transceiver 101, one or more acceleration measurements indicative of whether a shock to the transceiver 101 has occurred, and/or one or more temperature measurements indicative of the temperature of the transceiver 101. In some non-limiting embodiments, the one or more environmental sensors 930 of the transceiver 101 may generate the one or more environmental measurements. In some non-limiting embodiments, the one or more environmental sensors 930 may include one or more posture sensors 110, one or more pressure sensors 111, one or more shock sensors 113, and/or one or more temperature sensors 105. In some non-limiting embodiments, the transceiver 101 may additionally or alternatively receive one or more of the environmental measurements from a device external to the transceiver 101 (e.g., the display device 102).

In some embodiments, the process 300 may include a step 306 in which the transceiver 101 adjusts one or more sensor measurements received from the sensor 100. For example, in some embodiments, the one or more sensor measurements may include one or more temperature measurements, and step 306 may include adjusting one or more temperature measurements from the sensor 100. In some embodiments, a temperature measurement may be adjusted to be an estimate of the temperature of the analyte indicator 206, and the estimate may compensate for temperature lag. In some embodiments, adjusting a temperature measurement received from the sensor 100 may include calculating a rate of change of the temperature of the sensor 100 ($T_S\_ROC$) and calculating an adjusted temperature based on one or more of the received temperature measurement and the calculated $T_S\_ROC$.

In some non-limiting embodiments, the transceiver 101 may adjust one or more sensor measurements based on one or more environmental measurements. For example, in some embodiments, the one or more sensor measurements may include one or more temperature measurements, and step 306 may include adjusting one or more temperature measurements from the sensor 100 based on at least one or temperature measurements of the one or more environmental measurements (e.g., one or more temperature measurements generated by the one or more temperature sensors 105 of the transceiver 101). In some embodiments, a temperature measurement may be adjusted to be an estimate of the temperature of the analyte indicator 206, and the estimate may compensate for temperature lag. In some embodiments, adjusting a temperature measurement received from the sensor 100 may include calculating a rate of change of the temperature of the sensor 100 ($T_S\_ROC$), calculating a rate of change of the temperature of the transceiver 101 ($T_T\_ROC$), and calculating an adjusted temperature based one or more of a temperature measurement received from the sensor 100, the calculated $T_S\_ROC$, a temperature measurement generated by a temperature sensor 105, and the calculated $T_T\_ROC$.

In some embodiments, the process 300 may include a step 308 in which the transceiver 101 calculates first medium analyte level (e.g., an ISF analyte level) using the one or more sensor measurements received from the sensor 100. In some embodiments, one or more of the sensor measurements used to calculate the first medium analyte level may have been adjusted in step 306. In some embodiments, the first medium analyte level may be a measurement of the amount or concentration of the analyte in the first medium (e.g., interstitial fluid) in proximity to the analyte sensor 100. In some non-limiting embodiments, calculation of the first medium analyte level may include, for example and without limitation, some or all of the features described in U.S. application Ser. No. 13/937,871, filed on Jul. 9, 2013, now U.S. Pat. No. 9,414,775, which is incorporated by reference herein in its entirety.

In some embodiments, the process 300 may include a step 310 in which the transceiver 101 calculates a first medium analyte level rate of change ("M1_ROC"). In some embodiments, the transceiver 101 may calculate the M1_ROC using at least the first medium analyte level calculated in step 308 and one or more previously calculated first medium analyte levels (e.g., one or more first medium analyte levels calculated using previously received sensor measurements).

In some embodiments, the process 300 may include a step 312 in which the transceiver 101 adjusts a conversion function used to calculate a second medium analyte level (e.g., a blood analyte level) based on one or more environmental measurements generated by the one or more environmental sensors 930. In some non-limiting embodiments, the transceiver 101 may adjust the conversion function by adjusting one or more parameters (e.g., one or more of the analyte diffusion rate and analyte consumption rate parameters) of the conversion function. In some alternative embodiments, in step 312, the transceiver 101 may select one of a plurality of conversion functions based on one or more environmental measurements (e.g., one or more environmental measurements generated by the one or more environmental sensors 930).

In some embodiments, the process 300 may include a step 314 in which the transceiver 101 calculates a second medium analyte level (e.g., a blood analyte level). In some embodiments, the transceiver 101 may calculate the second medium analyte level by performing a lag compensation. In some embodiments, the transceiver 101 may calculate the second medium analyte level using at least the first medium analyte level and the M1_ROC calculated in steps 308 and 310, respectively. In some embodiments, the transceiver 101 may calculate the second medium analyte level using a conversion function. In some non-limiting embodiments, the conversion function used in step 314 may have been adjusted (or selected) in step 312.

In some non-limiting embodiments, the process 300 may include a step 316 of displaying the calculated second medium analyte level. In some embodiments, the step 316 may include displaying the calculated second medium analyte level on a display of the transceiver 101. In some embodiments, the step 316 may additionally or alternatively include the transceiver 101 conveying the calculated second medium analyte level to a display device (e.g., display device 102) for display. In some non-limiting embodiments, the transceiver 101 may convey the calculated second medium analyte level to the display device 102 via wired or wireless communication using the display interface device 106. In some embodiments, the display device 102 may be configured to receive and display the conveyed second medium analyte level.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, although the invention is described above in the context of an analyte monitoring system that calculates blood analyte levels indirectly using measurements of analyte levels in interstitial fluid, the invention is applicable to any monitoring system that calculates levels in a first medium using measurements of levels in a second medium.

What is claimed is:

1. An analyte monitoring system comprising:
   an analyte sensor comprising: (i) one or more sensors configured to generate sensor measurements indicative of an analyte level in a first medium, wherein the one or more sensors include a temperature transducer configured to generate a sensor temperature measurement, and the sensor measurements include the sensor temperature measurement, and (ii) a transceiver interface configured to convey the sensor measurements;
   a temperature sensor configured to generate a temperature measurement; and
   a transceiver comprising a sensor interface configured to receive the sensor measurements conveyed by the analyte sensor, wherein the transceiver is configured to adjust the sensor temperature measurement and calculate an analyte level in a second medium using at least the adjusted sensor temperature measurement and one or more of the sensor measurements, and adjusting the sensor temperature measurement comprises:
      calculating a rate of change of the temperature of the analyte sensor using at least the sensor temperature measurement and one or more sensor temperature measurements received previously from the analyte sensor;
      calculating a rate of change of the temperature of the transceiver using at least the temperature measurement generated by the temperature sensor and one or more temperature measurements generated previously by the temperature sensor; and
      calculating the adjusted sensor temperature measurement using at least the sensor temperature measurement, the calculated rate of change of the temperature of the analyte sensor, the temperature measurement generated by the temperature sensor, and the calculated rate of change of the temperature of the transceiver.

2. The analyte monitoring system of claim 1, wherein the analyte sensor further comprises a housing and an analyte indicator on or in at least a portion of an exterior surface of the sensor housing.

3. The analyte monitoring system of claim 2, wherein the sensor temperature measurement is a measurement of temperature inside the housing of the analyte sensor, and the adjusted sensor temperature measurement is an estimate of a temperature of the analyte indicator.

4. The analyte monitoring system of claim 3, wherein the adjusted sensor temperature measurement accounts for a lag between the temperature inside the housing of the analyte sensor and the temperature of the analyte indicator.

5. The analyte monitoring system of claim 2, wherein the one or more sensors of the analyte sensor further include: (i) a light source configured to emit excitation light that interacts with indicator molecules of the analyte indicator and causes the indicator molecules to emit emission light and (ii) a photodetector configured to generate a signal indicative of a level of the emission light emitted by the indicator molecules, and the sensor measurements further include a measurement of the signal generated by the photodetector.

6. The analyte monitoring system of claim 1, wherein calculating the analyte level in the second medium using at least the adjusted sensor temperature measurement and the one or more of the sensor measurements comprises calculating an analyte level in the first medium using at least the adjusted sensor temperature measurement and the one or more of the sensor measurements and calculating the analyte level in the second medium using at least the calculated analyte level in the first medium.

7. An analyte monitoring system comprising:
an analyte sensor comprising:
  (i) one or more sensors configured to generate sensor measurements indicative of an analyte level in a first medium, wherein the one or more sensors include a temperature transducer configured to generate a sensor temperature measurement, and the sensor measurements include the sensor temperature measurement;
  (ii) a housing, wherein the sensor temperature measurement is a measurement of temperature inside the housing of the analyte sensor;
  (iii) an analyte indicator on or in at least a portion of an exterior surface of the housing; and
  (iv) a transceiver interface configured to convey the sensor measurements; and
a transceiver comprising a sensor interface configured to receive the sensor measurements conveyed by the analyte sensor, wherein the transceiver is configured to:
  adjust the sensor temperature measurement, wherein the adjusted sensor temperature measurement is an estimate of a temperature of the analyte indicator, the adjusted sensor temperature measurement accounts for a lag between the temperature inside the housing of the analyte sensor and the temperature of the analyte indicator, and adjusting the sensor temperature measurement comprises:
    calculating a rate of change of the temperature of the analyte sensor using at least the sensor temperature measurement and one or more sensor temperature measurements received previously from the analyte sensor; and
    calculating the adjusted sensor temperature measurement using at least the sensor temperature measurement and the calculated rate of change of the temperature of the analyte sensor; and
  calculate an analyte level in a second medium using at least the adjusted sensor temperature measurement and one or more of the sensor measurements.

8. The analyte monitoring system of claim 1, wherein the adjusted sensor temperature measurement accounts for a lag between a temperature measured by the temperature sensor and the temperature of the analyte indicator.

9. The analyte monitoring system of claim 7, wherein the sensor interface of the transceiver is configured to receive wirelessly the sensor measurements conveyed by the analyte sensor.

10. The analyte monitoring system of claim 7, wherein the analyte sensor is a fully implantable sensor, and the transceiver is a handheld or body-worn transceiver.

11. The analyte monitoring system of claim 7, wherein the adjusted sensor temperature measurement is calculated as $\tau^* dT_S/dt + T_S$, $T_S$ is the temperature of the analyte sensor, $\tau$ is the rate constant between subcutaneous tissue and the analyte sensor, $dT_S/dt$ is the derivative of the temperature of the analyte sensor with respect to time, the sensor temperature measurement is used as the temperature of the analyte sensor, and the calculated rate of change of the temperature of the analyte sensor is used as the derivative of the temperature of the analyte sensor with respect to time.

12. The analyte monitoring system of claim 7, further comprising a temperature sensor configured to generate a temperature measurement, wherein the transceiver is configured to adjust the sensor temperature measurement using at least the temperature measurement generated by the temperature sensor.

13. The analyte monitoring system of claim 12, wherein the transceiver comprises the temperature sensor.

14. The analyte monitoring system of claim 12, wherein adjusting the sensor temperature measurement comprises calculating a rate of change of the temperature of the transceiver using at least the temperature measurement generated by the temperature sensor and one or more temperature measurements generated previously by the temperature sensor.

15. The analyte monitoring system of claim 14, wherein adjusting the sensor temperature measurement comprises calculating the adjusted sensor temperature measurement using at least the temperature measurement generated by the temperature sensor and the calculated rate of change of the temperature of the transducer.

16. The analyte monitoring system of claim 15, wherein calculating the adjusted sensor temperature measurement uses at least the sensor temperature measurement, the calculated rate of change of the temperature of the analyte sensor, the temperature measurement generated by the temperature sensor, and the calculated rate of change of the temperature of the transducer.

17. The analyte monitoring system of claim 7, wherein calculating the analyte level in the second medium using at least the adjusted sensor temperature measurement and the one or more of the sensor measurements comprises calculating an analyte level in the first medium using at least the adjusted sensor temperature measurement and the one or more of the sensor measurements and calculating the analyte level in the second medium using at least the calculated analyte level in the first medium.

18. The analyte monitoring system of claim 7, wherein the one or more sensors of the analyte sensor further include: (i) a light source configured to emit excitation light that interacts with indicator molecules of the analyte indicator and causes the indicator molecules to emit emission light and (ii) a photodetector configured to generate a signal indicative of a level of the emission light emitted by the indicator molecules, and the sensor measurements further include a measurement of the signal generated by the photodetector.

19. A method comprising:
using one or more sensors of an analyte sensor to generate sensor measurements indicative of an analyte level in a first medium, wherein the one or more sensors include a temperature transducer, and the sensor measurements include a sensor temperature measurement generated by the temperature transducer;
using a transceiver interface of the analyte sensor to convey the sensor measurements;
using a sensor interface of a transceiver to receive the sensor measurements conveyed by the analyte sensor;
using a temperature sensor to generate a temperature measurement;
using the transceiver to adjust the sensor temperature measurement, wherein adjusting the sensor temperature measurement comprises:
calculating a rate of change of the temperature of the analyte sensor using at least the sensor temperature measurement and one or more sensor temperature measurements received previously from the analyte sensor;
calculating a rate of change of the temperature of the transceiver using at least the temperature measurement generated by the temperature sensor and one or more temperature measurements generated previously by the temperature sensor; and
calculating the adjusted sensor temperature measurement using at least the sensor temperature measurement, the calculated rate of change of the temperature of the analyte sensor, the temperature measurement generated by the temperature sensor, and the calculated rate of change of the temperature of the transceiver; and
using the transceiver to calculate an analyte level in a second medium using at least the adjusted sensor temperature measurement and one or more of the sensor measurements.

20. The method of claim 19, wherein the analyte sensor further comprises a housing and an analyte indicator on or in at least a portion of an exterior surface of the sensor housing, the sensor temperature measurement is a measurement of temperature inside the housing of the analyte sensor, and the adjusted sensor temperature measurement is an estimate of a temperature of the analyte indicator.

21. The method of claim 20, wherein the adjusted sensor temperature measurement accounts for a lag between the temperature inside the housing of the analyte sensor and the temperature of the analyte indicator.

22. The method of claim 20, wherein the one or more sensors of the analyte sensor further include a light source and a photodetector, and using the one or more sensors to generate the sensor measurements comprises:
using the light source to emit excitation light that interacts with indicator molecules of the analyte indicator and causes the indicator molecules to emit emission light; and
using the photodetector to generate a signal indicative of a level of the emission light emitted by the indicator molecules;
wherein the sensor measurements further include a measurement of the signal generated by the photodetector.

23. The method of claim 19, wherein calculating the analyte level in the second medium using at least the adjusted sensor temperature measurement and the one or more of the sensor measurements comprises calculating an analyte level in the first medium using at least the adjusted sensor temperature measurement and the one or more of the sensor measurements and calculating the analyte level in the second medium using at least the calculated analyte level in the first medium.

24. The method of claim 19, wherein the adjusted sensor temperature measurement accounts for a lag between a temperature measured by the temperature sensor and the temperature of the analyte indicator.

25. The method of claim 19, wherein the transceiver interface of the analyte sensor conveys wirelessly the sensor measurements, and the sensor interface of the transceiver receives wirelessly the sensor measurements.

26. The method of claim 19, wherein the analyte sensor is a fully implantable sensor, and the transceiver is a handheld or body-worn transceiver.

27. A method comprising:
using one or more sensors of an analyte sensor to generate sensor measurements indicative of an analyte level in a first medium, wherein the sensors include a temperature transducer, the sensor measurements include a sensor temperature measurement generated by the temperature transducer, and the sensor temperature measurement is a measurement of temperature inside a housing of the analyte sensor;
using a transceiver interface of the analyte sensor to convey the sensor measurements;
using a sensor interface of a transceiver to receive the sensor measurements conveyed by the analyte sensor;
using the transceiver to adjust the sensor temperature measurement, wherein the adjusted sensor temperature measurement is an estimate of a temperature of an analyte indicator on or in at least a portion of an exterior surface of the housing of the analyte sensor, the adjusted sensor temperature measurement accounts for a lag between the temperature inside the housing of the analyte sensor and the temperature of the analyte indicator, and adjusting the sensor temperature measurement comprises:
calculating a rate of change of the temperature of the analyte sensor using at least the sensor temperature measurement and one or more sensor temperature measurements received previously from the analyte sensor; and
calculating the adjusted sensor temperature measurement using at least the sensor temperature measurement and the calculated rate of change of the temperature of the analyte sensor; and
using the transceiver to calculate an analyte level in a second medium using at least the adjusted sensor temperature measurement and one or more of the sensor measurements.

28. The analyte monitoring system of claim 1, wherein the sensor interface of the transceiver is configured to receive wirelessly the sensor measurements conveyed by the analyte sensor.

29. The analyte monitoring system of claim 1, wherein the analyte sensor is a fully implantable sensor, and the transceiver is a handheld or body-worn transceiver.

30. The method of claim 27, wherein the transceiver interface of the analyte sensor conveys wirelessly the sensor measurements, and the sensor interface of the transceiver receives wirelessly the sensor measurements.

31. The method of claim 27, wherein the analyte sensor is a fully implantable sensor, and the transceiver is a handheld or body-worn transceiver.

32. The method of claim 27, wherein calculating the analyte level in the second medium using at least the adjusted sensor temperature measurement and the one or more of the sensor measurements comprises calculating an analyte level in the first medium using at least the adjusted sensor temperature measurement and the one or more of the sensor measurements and calculating the analyte level in the second medium using at least the calculated analyte level in the first medium.

33. The method of claim 27, wherein the adjusted sensor temperature measurement is calculated as $\tau^* dT_S/dt + T_S$, $T_S$ is the temperature of the analyte sensor, $\tau$ is the rate constant between subcutaneous tissue and the analyte sensor, $dT_S/dt$ is the derivative of the temperature of the analyte sensor with respect to time, the sensor temperature measurement is used as the temperature of the analyte sensor, and the calculated rate of change of the temperature of the analyte sensor is used as the derivative of the temperature of the analyte sensor with respect to time.

34. The method of claim 27, wherein the one or more sensors of the analyte sensor further include a light source and a photodetector, and using the one or more sensors to generate the sensor measurements comprises:

using the light source to emit excitation light that interacts with indicator molecules of the analyte indicator and causes the indicator molecules to emit emission light; and using the photodetector to generate a signal indicative of a level of the emission light emitted by the indicator molecules;

wherein the sensor measurements further include a measurement of the signal generated by the photodetector.

* * * * *

UNITED STATES PATENT AND TRADEMARK OFFICE
CERTIFICATE OF CORRECTION

| | |
|---|---|
| PATENT NO. | : 12,016,684 B2 |
| APPLICATION NO. | : 16/671291 |
| DATED | : June 25, 2024 |
| INVENTOR(S) | : DeHennis et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 843 days.

Signed and Sealed this
Twelfth Day of August, 2025

Coke Morgan Stewart
*Acting Director of the United States Patent and Trademark Office*